US009526581B2

(12) United States Patent
Bodduluri et al.

(10) Patent No.: US 9,526,581 B2
(45) Date of Patent: Dec. 27, 2016

(54) AUTOMATED SYSTEM AND METHOD FOR HARVESTING OR IMPLANTING FOLLICULAR UNITS

(71) Applicant: Restoration Robotics, Inc., San Jose, CA (US)

(72) Inventors: Mohan Bodduluri, Palo Alto, CA (US); Philip L. Gildenberg, Houston, TX (US); Donald E. Caddes, Menlo Park, CA (US)

(73) Assignee: Restoration Robotics, Inc., San Jose, CA (US)

( * ) Notice: Subject to any disclaimer, the term of this patent is extended or adjusted under 35 U.S.C. 154(b) by 313 days.

(21) Appl. No.: 14/177,462

(22) Filed: Feb. 11, 2014

(65) Prior Publication Data

US 2014/0155912 A1 Jun. 5, 2014

Related U.S. Application Data

(63) Continuation of application No. 13/112,171, filed on May 20, 2011, now Pat. No. 8,690,894, which is a
(Continued)

(51) Int. Cl.
A61B 34/30 (2016.01)
A61B 19/00 (2006.01)
(Continued)

(52) U.S. Cl.
CPC ......... *A61B 19/22* (2013.01); *A61B 17/32053* (2013.01); *A61B 17/3468* (2013.01);
(Continued)

(58) Field of Classification Search
CPC .............. A61B 19/22; A61B 17/32053; A61B 17/3468; A61B 19/52; A61B 19/2203; A61B 19/50; A61B 19/5212; A61B 2017/00752; A61B 2019/5227; A61M 37/0076
(Continued)

(56) References Cited

U.S. PATENT DOCUMENTS 2,667,879 A 2/1954 Mann et al.
3,867,942 A 2/1975 Bellantoni et al.
(Continued)

FOREIGN PATENT DOCUMENTS

DE 10249786 5/2004
WO WO 98/25666 6/1998

OTHER PUBLICATIONS

Website, http://www.medicamat.com/materiel/hair-transplant/omnigraft.html?L=1, Medicamat, Medical and Surgical Devices, Cosmetic Products, Hair Transplant/Omnigraft, accessed on Aug. 8, 2007, (1 page).
(Continued)

*Primary Examiner* — Katrina Stransky
(74) *Attorney, Agent, or Firm* — Lena I. Vinitskaya; Sharon Upham

(57) ABSTRACT

Automated systems and methods for operating a procedure tool to perform a procedure (for example, hair transplantation) on a body are provided. One or more mechanisms are configured to produce a combination movement of the procedure tool in response to control signals. A force sensor monitors resistance as the tool moves and transmits information from the force sensor to a computer. Movement of the procedure tool is controlled at least in part based on information from the force sensor.

25 Claims, 28 Drawing Sheets

Related U.S. Application Data continuation of application No. 11/380,907, filed on Apr. 28, 2006, now Pat. No. 7,962,192.

(60) Provisional application No. 60/722,521, filed on Sep. 30, 2005, provisional application No. 60/753,602, filed on Dec. 22, 2005, provisional application No. 60/764,173, filed on Jan. 31, 2006.

(51) Int. Cl.
| | |
|---|---|
| *A61B 17/3205* | (2006.01) |
| *A61B 17/34* | (2006.01) |
| *A61B 17/00* | (2006.01) |
| *A61M 37/00* | (2006.01) |

(52) U.S. Cl.
CPC ............ *A61B 34/70* (2016.02); *A61B 90/36* (2016.02); *A61B 34/10* (2016.02); *A61B 34/30* (2016.02); *A61B 90/361* (2016.02); *A61B 2017/00752* (2013.01); *A61B 2090/064* (2016.02); *A61B 2090/371* (2016.02); *A61M 37/0076* (2013.01)

(58) Field of Classification Search
USPC .................................................. 606/130, 187
See application file for complete search history.

(56) References Cited

U.S. PATENT DOCUMENTS

| | | | |
|---|---|---|---|
| 4,004,592 A | 1/1977 | Yamada | |
| 4,126,124 A * | 11/1978 | Miller ..................... | A61F 2/10 606/187 |
| 4,160,453 A | 7/1979 | Miller | |
| 4,451,254 A | 5/1984 | Dinius et al. | |
| 4,476,864 A | 10/1984 | Tezel | |
| 4,479,291 A | 10/1984 | Yamada | |
| 4,716,901 A | 1/1988 | Jackson et al. | |
| 4,751,927 A | 6/1988 | Yamada et al. | |
| 4,768,517 A | 9/1988 | Joachim | |
| 4,807,163 A | 2/1989 | Gibbons | |
| 4,969,903 A | 11/1990 | Valle | |
| 4,980,971 A | 1/1991 | Bartschat et al. | |
| 5,036,860 A | 8/1991 | Leigh et al. | |
| 5,050,608 A | 9/1991 | Watanabe et al. | |
| 5,078,140 A | 1/1992 | Kwoh | |
| 5,183,053 A | 2/1993 | Yeh et al. | |
| 5,230,623 A | 7/1993 | Guthrie et al. | |
| 5,251,127 A | 10/1993 | Raab | |
| 5,331,472 A | 7/1994 | Rassman | |
| 5,395,368 A | 3/1995 | Ellman et al. | |
| 5,417,683 A | 5/1995 | Shiao | |
| 5,439,475 A | 8/1995 | Bennett | |
| 5,449,370 A | 9/1995 | Vaitekunas | |
| 5,483,961 A | 1/1996 | Kelly et al. | |
| 5,490,850 A | 2/1996 | Ellman et al. | |
| 5,562,613 A | 10/1996 | Kaldany | |
| 5,578,054 A | 11/1996 | Arnold | |
| 5,584,841 A | 12/1996 | Rassman | |
| 5,584,851 A | 12/1996 | Banuchi | |
| 5,611,810 A | 3/1997 | Arnold et al. | |
| 5,611,811 A | 3/1997 | Goldberg | |
| 5,662,661 A | 9/1997 | Boudjema | |
| 5,693,064 A | 12/1997 | Arnold | |
| 5,733,278 A | 3/1998 | Slatkine et al. | |
| 5,749,362 A | 5/1998 | Funda et al. | |
| 5,782,843 A | 7/1998 | Aasberg | |
| 5,782,851 A | 7/1998 | Rassman | |
| 5,782,853 A | 7/1998 | Zeevi et al. | |
| 5,792,163 A | 8/1998 | Hitzig | |
| 5,792,169 A | 8/1998 | Markman | |
| 5,817,105 A | 10/1998 | Van Der Brug | |
| 5,817,120 A | 10/1998 | Rassman | |
| 5,827,217 A | 10/1998 | Silver et al. | |
| 5,827,297 A | 10/1998 | Boudjema | |
| 5,858,019 A | 1/1999 | Ashraf | |
| 5,865,744 A | 2/1999 | Lemelson | |
| 5,873,888 A | 2/1999 | Costanzo | |
| 5,893,853 A | 4/1999 | Arnold | |
| 5,895,403 A | 4/1999 | Collinsworth | |
| 5,899,916 A | 5/1999 | Casparian | |
| 5,901,199 A | 5/1999 | Murphy et al. | |
| 5,951,572 A | 9/1999 | Markman | |
| 5,961,529 A | 10/1999 | Arnold | |
| 5,984,936 A | 11/1999 | Mangubat et al. | |
| 5,989,273 A | 11/1999 | Arnold | |
| 5,989,279 A | 11/1999 | Rassman | |
| 5,997,550 A | 12/1999 | Russell | |
| 6,013,087 A | 1/2000 | Adams et al. | |
| 6,027,512 A | 2/2000 | Bridges | |
| 6,056,736 A | 5/2000 | Markman | |
| 6,059,807 A | 5/2000 | Boudjema | |
| 6,110,189 A | 8/2000 | Markman | |
| 6,120,521 A | 9/2000 | Casparian | |
| 6,341,831 B1 | 1/2002 | Weber et al. | |
| 6,445,943 B1 | 9/2002 | Ferre et al. | |
| 6,461,369 B1 | 10/2002 | Kim | |
| 6,484,049 B1 | 11/2002 | Seeley et al. | |
| 6,547,782 B1 | 4/2003 | Taylor | |
| 6,572,625 B1 | 6/2003 | Rassman | |
| 6,585,746 B2 | 7/2003 | Gildenberg | |
| 6,694,167 B1 | 2/2004 | Ferre et al. | |
| 6,917,702 B2 | 7/2005 | Beardsley | |
| 6,973,931 B1 | 12/2005 | King | |
| 7,083,611 B2 | 8/2006 | Lemchen | |
| 7,217,266 B2 | 5/2007 | Anderson et al. | |
| 7,277,120 B2 | 10/2007 | Gere et al. | |
| 8,690,894 B2* | 4/2014 | Bodduluri ........ | A61B 17/32053 606/133 |
| 2001/0034534 A1 | 10/2001 | Transue | |
| 2002/0103500 A1 | 8/2002 | Gildenberg | |
| 2002/0133149 A1 | 9/2002 | Bessette | |
| 2002/0151784 A1 | 10/2002 | Mizoguchi et al. | |
| 2003/0040766 A1 | 2/2003 | Werner | |
| 2003/0097144 A1 | 5/2003 | Lee | |
| 2003/0181801 A1 | 9/2003 | Lasser et al. | |
| 2003/0181936 A1 | 9/2003 | Trautman et al. | |
| 2004/0034282 A1 | 2/2004 | Quaid, III | |
| 2004/0092924 A1 | 5/2004 | Vasa | |
| 2004/0116942 A1 | 6/2004 | Feller | |
| 2004/0162505 A1 | 8/2004 | Kaplan et al. | |
| 2004/0193203 A1* | 9/2004 | Pak ..................... | A61B 17/3468 606/187 |
| 2004/0204700 A1* | 10/2004 | Weaver ................. | A61M 5/427 604/500 |
| 2004/0220589 A1 | 11/2004 | Feller | |
| 2004/0225314 A1 | 11/2004 | Fukuyama | |
| 2004/0243147 A1* | 12/2004 | Lipow ..................... | A61B 90/36 606/130 |
| 2006/0079816 A1 | 4/2006 | Barthe et al. | |
| 2007/0038236 A1 | 2/2007 | Cohen | |
| 2007/0255293 A1 | 11/2007 | Corre | |
| 2007/0293884 A9 | 12/2007 | Cole et al. | |
| 2008/0002809 A1 | 1/2008 | Bodduluri | |
| 2008/0242990 A1 | 10/2008 | Zanelli et al. | |
| 2010/0125287 A1 | 5/2010 | Cole et al. | |

OTHER PUBLICATIONS

Website, http://www.medicamat.com/materiel/hair-transplant/punchhairmatic.html?L=1, Medicamat, Medical and Surgical Devices, Cosmetic Products, Hair Transplant/Punch Hair Matic, accessed on Aug. 8, 2007, (1 page).

Website, http://www.medicamat.com/materiel/hair-transplant/omnigraft/case-study.html?L=1, Omnigraft, Medicamat, Medical and Surgical Devices, Cosmetic Products, Hair Transplant/Omnigraft/Case Study, accessed on Aug. 8, 2007, (4 pages).

Website, http://www.medicamat.com/materiel/hair-transplant/punchhairmatic/case-study.html?L=1, Medicamat, Medical and Surgical Devices, Cosmetic Products, Hair Transplant/Punch Hair

(56) References Cited

OTHER PUBLICATIONS

Matic/Case Study, Website, http://www.medicamat.com/materiel/hair-tr, (3 pages).
Annex to form PCT/ISA/206, Communication Relating to the Results of the Partial International Search, attached to PCT Invitation to Pay Additional Fees, PCT/ISA/206, for PCT/US2006/0038002, Applicant Restoration Robotics, Inc., dated Jan. 25, 2007, (5 pages).
"Automated Hair Restoration System, OmniGraft", Brochure—Medicamat, (4 pages).
Communication from EPC mailed Jan. 5, 2009 in the Application No. 06804246.4, Applicant Restoration Robotics, Inc., Jan. 5, 2009, (3 pages).
Non-Final Office Action mailed Jan. 16, 2013, in relation to commonly assigned U.S. Appl. No. 13/112,171, Jan. 16, 2013, (15 pages).
Office Action dated Dec. 11, 2008, for U.S. Appl. No. 11/380,907, filed Apr. 28, 2006, Applicant Restoration Robotics, Inc.
PCT International Search Report for PCT/US2006/0038002, Applicant Restoration Robotics, Inc., forms PCT/ISA/210 and 220, dated Apr. 11, 2007, (7 pages).
PCT Written Opinion of the International Search Report Authority for PCT/US2006/0038002, Applicant Restoration Robotics, Inc., Form PCT/ISA/237, dated Apr. 11 2007, (7 pages).
"Punch-Hair-Matic A New Robot to Fight Baldness", Brochure—Medicamat, (3 pages).
Forsyth, et al., "Computer Vision, A Modern Approach", Cover page, publication pages, and Chapters 10 & 11, Pearson Education, Inc., 2003, pp. 215-250.
Harris, "New Methodology and Instrumentation for Follicular Unit Extraction: Lower Follicle Transection Rates and Expanded Patient Candidacy", Dermatol Surg 32, Jan. 2006.
Inaba, et al., "Androgenetic Alopecia, Modern Concepts of Pathogenesis and Treatment, 29. Operative Treatment for Androgenetic Alopecia.", 1996, pp. 238-244, 309 (9 pages).
Jain, et al., "Machine Vision", Cover page, publication page, and Chapters 11 & 12. McGraw-Hill, Inc., 1995, pp. 289-364.
Konolige, et al., "SRI Small Vision System", SRI International—User's Manual Software Version 3.2g, Nov. 2004, (86 pages).
Lanfranco, et al., "Robotic Surgery : A Current Perspective", Annals of Surgery, vol. 239, No. 1,, Jan. 2004, pp. 14-21.
Riordan, "Implanting Hair is Tedious, Exacting Work—the Perfect Work for a Robot", The New York Times,, Sep. 15, 2003, (1 page).
Woodfill, et al., "The Tyzx DeapSea G2 Vision System, A Taskable, Embedded Stereo Camera", Proceedings of the IEEE Computer Society Workshop on Embedded Computer Vision, Conference on Computer Vision and Pattern Recognition, Jun. 2006, 5 pages.
Woodfill, et al., "Tyzx DeepSea High Speed Stereo Vision System", Proceedings of the IEEE Computer Society Workshop on Real Time 3-D Sensors and Their Use, Conference on Computer Vision and Pattern Recognition, (Washington, D.C.), Jun. 2004, 5 pages.

* cited by examiner

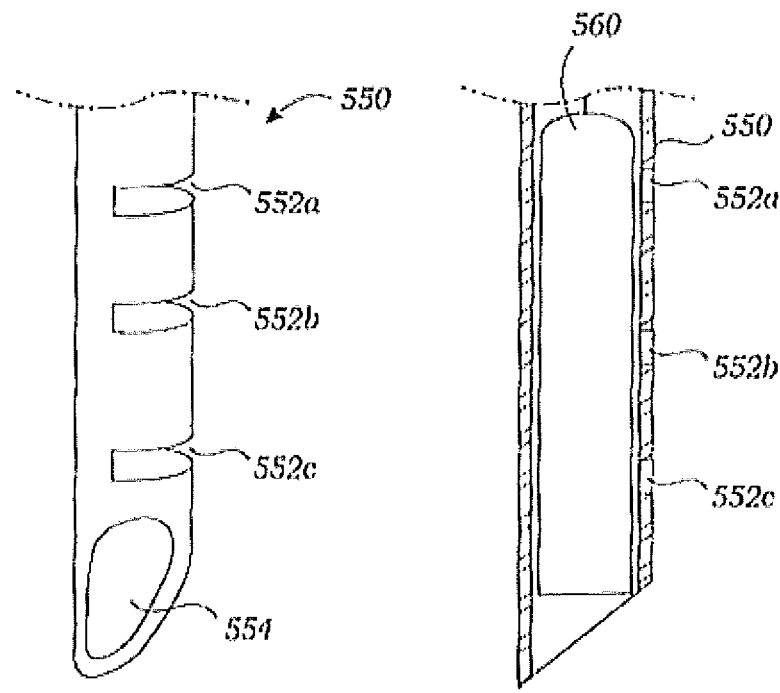
Fig. 31
Fig. 32A
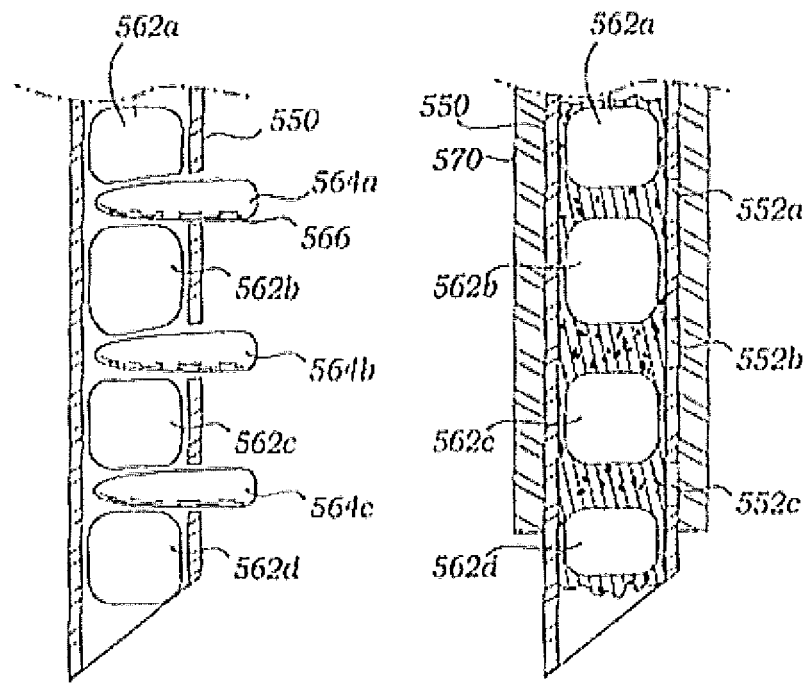
Fig. 32B
Fig. 32C

AUTOMATED SYSTEM AND METHOD FOR HARVESTING OR IMPLANTING FOLLICULAR UNITS

RELATED APPLICATION DATA

The present application is a continuation of U.S. patent application Ser. No. 13/112,171, entitled "Automated System for Harvesting or Implanting Follicular Units", filed May 20, 2011, which is a continuation of U.S. patent application Ser. No. 11/380,907, entitled "Systems and Methods for Aligning a Tool with a Desired Location or Object", filed Apr. 28, 2006, now U.S. Pat. No. 7,962,192 issued Jun. 14, 2011, which claims the benefit under 35 U.S.C. §119 to U.S. provisional patent application Ser. No. 60/722,521, filed Sep. 30, 2005, Ser. No. 60/753,602, filed Dec. 22, 2005, and 60/764,173, filed Jan. 31, 2006. The foregoing applications are all hereby incorporated by reference into the present application in their entirety.

FIELD OF INVENTION

This invention relates generally to an image-guided robotics system for performing precision diagnostic and therapeutic medical procedures.

BACKGROUND

U.S. Pat. No. 6,585,746 discloses a hair transplantation system utilizing a robot, including a robotic arm and a hair follicle introducer associated with the robotic arm. A video system is used to produce a three-dimensional virtual image of the patient's scalp, which is used to plan the scalp locations that are to receive hair grafts implanted by the follicle introducer under the control of the robotic arm. The entire disclosure of U.S. Pat. No. 6,585,746 is incorporated herein by reference.

SUMMARY

In accordance with a general aspect of the inventions disclosed herein, an automated system, such as an image-guided robotics system, is employed for performing precisely controlled diagnostic and therapeutic medical procedures, such as (by way of non-limiting examples) hair removal and/or transplantation, repetitive needle injections (e.g., for delivery of collagen fillers, melanocyte, tattoo ink), tattoo or mole removal, application of laser or radio frequency (RF) energy, cryogenic therapy (e.g., for mole or wart removal), patterned micro-tissue removal (e.g., as an alternative to a conventional "face lift" procedure), and any other procedure currently performed using human-controlled devices.

According to according to some embodiments, an automated system may also be employed for performing diagnostic evaluations, such as, e.g., obtaining precision image data for skin cancer screening, and performing ultrasound diagnostics. In various embodiments, the robotics system generally includes a robotic arm controlled by a system controller, an end-effecter assembly coupled to a distal (tool) end of the robotic arm, and an image acquisition system, including one or more high speed cameras coupled to the end-effecter assembly for acquiring images that are processed for providing control signals for movement of the robotic arm using a "visual-servoing" process.

In accordance with some embodiments of the invention, an automated system for harvesting or implanting follicular units is provided, the system including a moveable arm, a tool mounted on the moveable arm, one or more cameras mounted on the moveable arm, a processor configured to receive and process images acquired by the one or more cameras, and a controller operatively associated with the processor and configured to position the moveable arm based, at least in part, on processed images acquired by the one or more cameras, wherein the moveable arm is positionable such that the tool may be positioned at a desired orientation relative to an adjacent body surface.

By way of non-limiting example, the automated system may be a robotic system, wherein the moveable arm is a robotic arm, and wherein the processor and controller may be configured for positioning the tool by visual servoing of the robotic arm. In some embodiments, a single camera may be employed, wherein the processor is configured to register a reference coordinate system of the camera with a tool frame reference coordinate system of the robotic arm. For example, the processor may register the camera reference coordinate system with the tool frame reference coordinate system based on images of a fixed calibration target acquired as the robotic arm is moved along one or more axes of the tool frame reference coordinate system. By way of another example, a pair of cameras may be mounted to the robotic arm, wherein the processor is configured to register respective reference coordinate systems of the cameras with each other and with a tool frame reference coordinate system of the robotic arm. Again, the processor may register the respective camera reference coordinate systems with the tool frame reference coordinate system based on images of a fixed calibration target acquired as the robotic arm is moved along one or more axes of the tool frame reference coordinate system. By way of yet another example, the one or more cameras comprises respective first and second pairs of cameras mounted to the robotic arm, the first pair focused to acquire images of a first field of view, and the second pair focused to acquire images of a second field of view substantially narrower than the first field of view. In this embodiment, the processor may be configured to register respective reference coordinate systems of the first and second pairs of cameras with each other and with a tool frame reference coordinate system of the robotic arm. Again, the processor may register the respective camera reference coordinate systems with the tool frame reference coordinate system based on images of a fixed calibration target acquired as the robotic arm is moved along one or more axes of the tool frame reference coordinate system.

In various embodiments, the tool comprises one or both of a follicular unit harvesting tool and a follicular unit implantation tool. In various embodiments, the processor may be configured to identify approximate physical boundaries of a follicular unit in an image acquired by the one or more cameras. For example, the processor may be configured for identifying approximate physical boundaries of a follicular unit captured in an acquired image, including a subcutaneous base region embedded in the body surface and a distal tip region extending away from the body surface, wherein the images include subcutaneous images. In yet another embodiment, an air jet is provided on the moveable arm for directing an air stream at the body surface. In yet another embodiment, a user interface is provided for a user to input instructions to one or both of the processor and controller regarding one or more of a location, position, orientation, and depth of a follicular unit to be implanted.

In accordance with further embodiments, an automated system for harvesting or implanting follicular units includes a moveable arm, a tool mounted on the moveable arm, a pair of cameras, a processor configured to receive and process images acquired by the cameras, wherein the processor is configured to register respective reference coordinate systems of the cameras with each other, and a controller operatively associated with the processor and configured to position the moveable arm based, at least in part, on processed images acquired by the cameras, wherein the moveable arm is positionable such that the tool may be positioned at a desired orientation relative to an adjacent body surface. By way of non-limiting example, the automated system may be a robotic system, wherein the moveable arm is a robotic arm, and the processor is further configured to register the respective camera reference coordinate systems with a tool frame reference coordinate system of the robotic arm. In such embodiment, the processor and controller may be configured for positioning the tool by visual servoing of the robotic arm.

In accordance with yet further embodiments, an automated system for harvesting or implanting follicular units includes a moveable arm, a tool mounted on the moveable arm, first and second pairs of cameras mounted to the moveable arm, the first pair focused to acquire images of a first field of view, and the second pair focused to acquire images of a second field substantially narrower than the first field of view, a processor configured to receive and process images acquired by the respective pairs of cameras, wherein the processor is configured to register respective reference coordinate systems of the camera pairs with each other, and a controller operatively associated with the processor and configured to position the moveable arm based, at least in part, on processed images acquired by the respective pairs of cameras, and wherein the moveable arm is positionable such that the tool may be positioned at a desired orientation relative to an adjacent body surface. For example, the automated system may be a robotic system, wherein the moveable arm is a robotic arm, and the processor may be further configured to register the respective camera reference coordinate systems with a tool frame reference coordinate system of the robotic arm.

Other and further objects and advantages of the invention will become apparent from the following detailed description when read in view of the accompanying figures.

BRIEF DESCRIPTION OF THE DRAWINGS

The invention is illustrated by way of example and not limitation in the figures of the accompanying drawings, in which like references indicate similar elements, and in which:

FIG. 31 illustrates a needle assembly in accordance with still other embodiments.

FIGS. 32A-32C illustrate an exemplary method of using the needle assembly of FIG. 31 in accordance with some embodiments.

DETAILED DESCRIPTION OF THE ILLUSTRATED EMBODIMENTS

Figure 1:
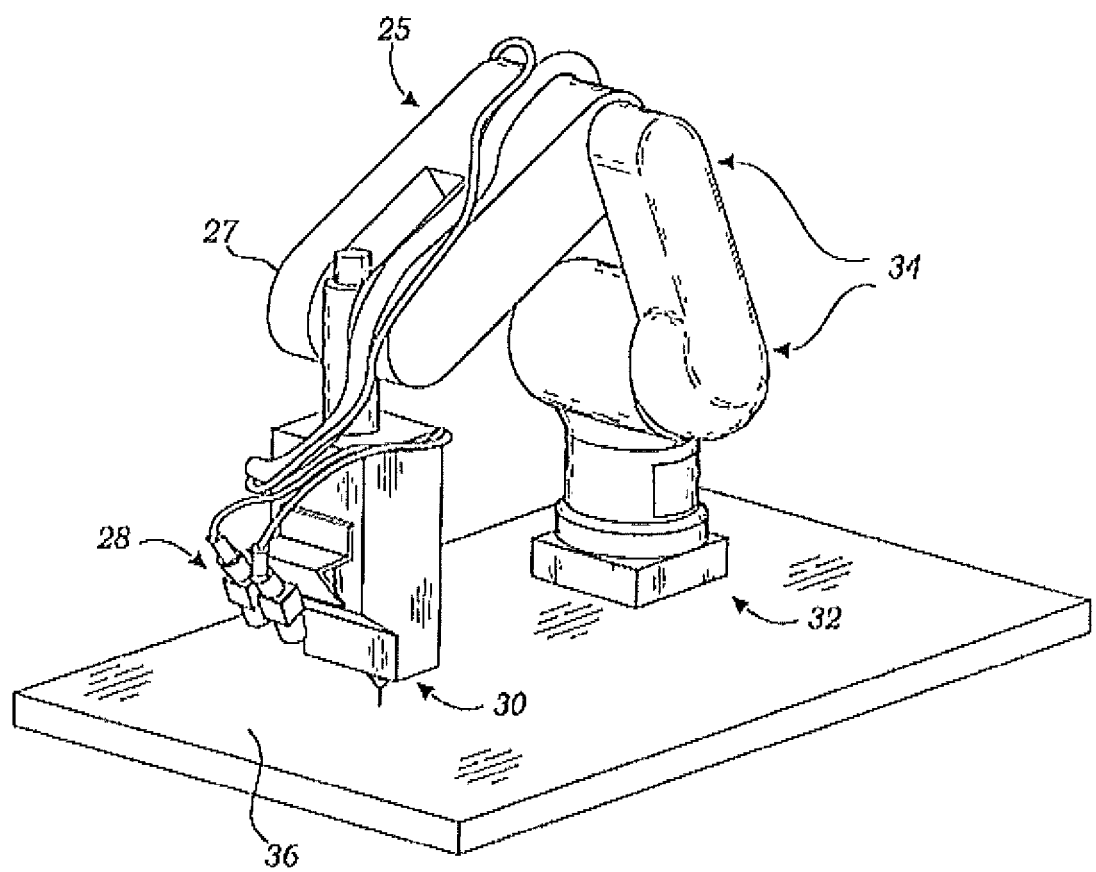
FIG. 1 is a photograph of an embodiment of an image-guided robotics system, including a robotic arm for positioning and orienting an end-effecter tool at targeted locations on the skin surface of a patient.

FIG. 1 depicts an image-guided robotics system 25, including a programmable robotic arm 27 of a type manufactured and distributed by Adept Technology, Inc. (www.adept.com). Another source of robotic arm assemblies suitable for embodiments of the invention are manufactured and distributed by Kuka Robot Group (www.kuka.com). The robotic arm 27 provides precisely controlled movement of a distal end plate (not seen in FIG. 1) in six degrees of freedom (x, y, z, co, p, r), as is well-known in the art. Such movement of the distal plate is provided with a high degree of repeatability and accuracy (e.g., to 20 microns) by respective motors and encoders located in respective arm joints 34 of the robotic arm 27.

Figure 2:
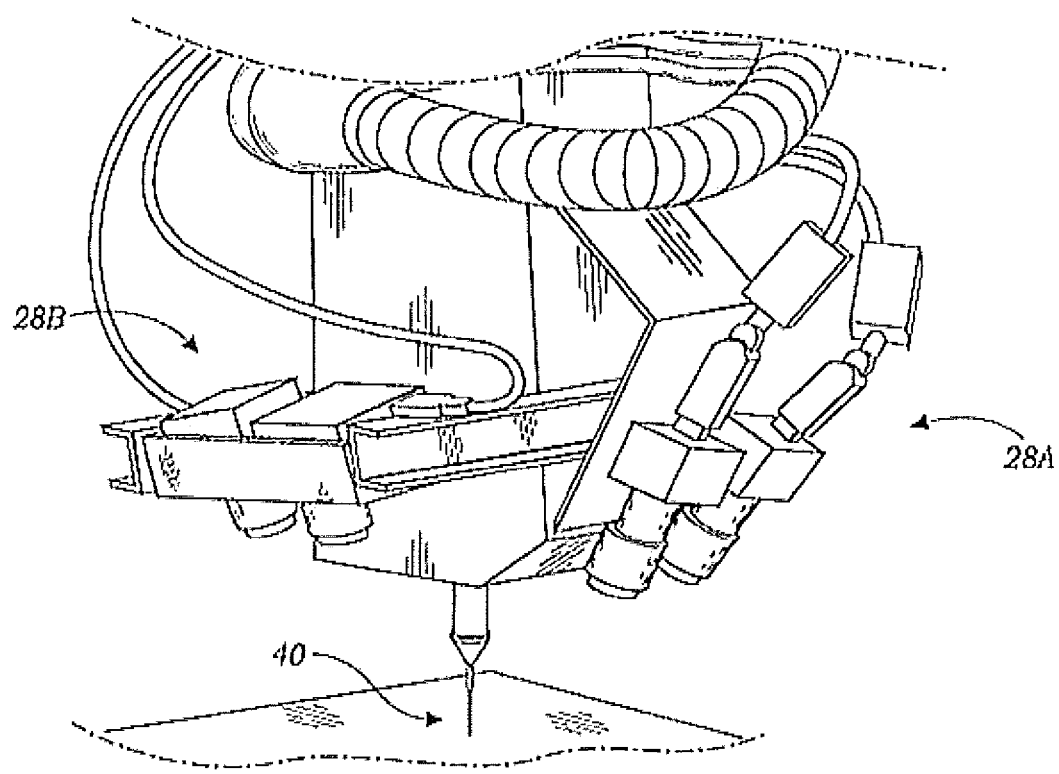
FIG. 2 is a photograph showing first and second stereo camera pairs secured to the robotic arm of FIG. 1, and used to capture image data from multiple fields-of-view for guiding movement of the robotic arm and an attached end-effecter tool assembly.
Figure 3:
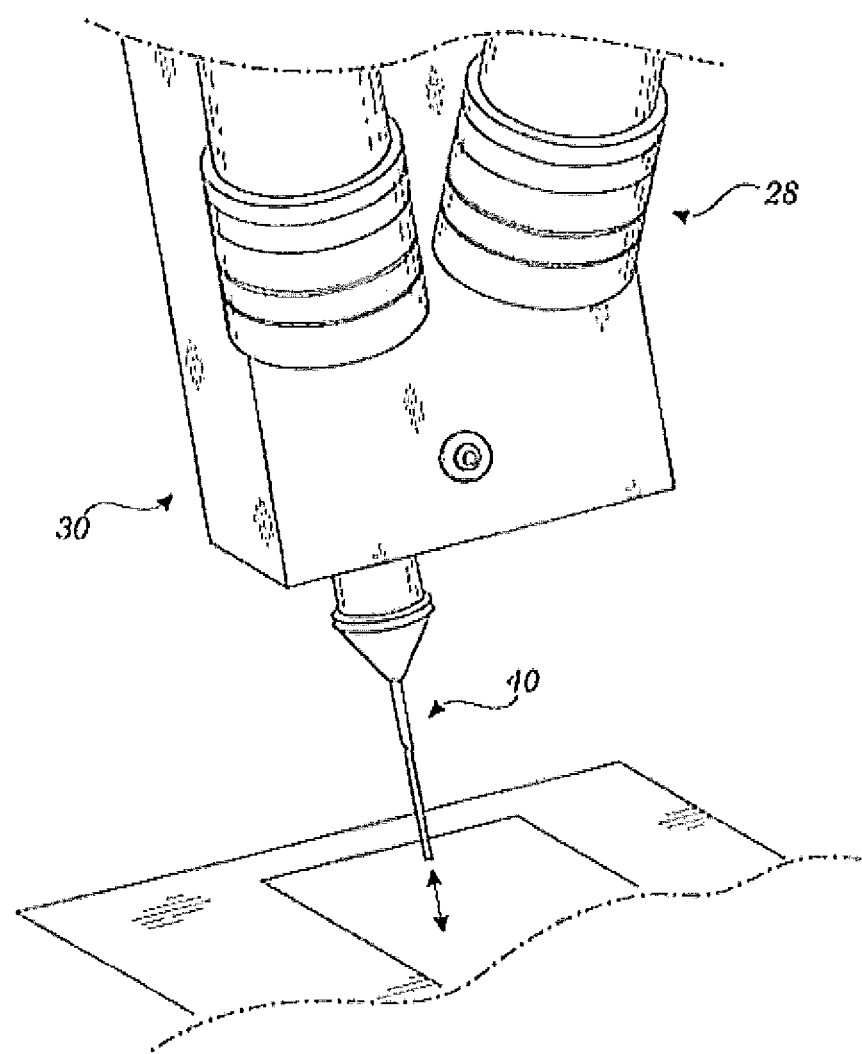
FIG. 3 is a close-up photograph of the system of FIG. 2, more clearly showing the end-effecter tool.

A variety of different end-effecter tools and/or assemblies may be attached to the distal end plate on the robotic arm 27 for performing various procedures on a human or animal patient. By way of example, the end-effecter assembly 30 shown in FIGS. 1-3 is designed for the harvesting and implantation of hair follicles from/in a human scalp. It will be appreciated that embodiments of the invention will employ many different types of end-effecter tools and assemblies for performing diagnostic and therapeutic medical procedures that take advantage of the ability of the robotic arm 27 to rapidly and precisely position the respective tool (e.g., needle) or assembly at desired locations at the skin surface of a patient. It will be appreciated that the end-effecter assemblies may themselves include moving, controllable parts. By way of example, one end-effecter assembly comprises a reciprocating needle used for delivering precisely targeted, repetitive injections through the dermis.

As described in greater detail herein, movement of the robotic arm 27 is governed by a system controller (not shown), in response to control signals derived from image data acquired by a pair of "stereo" cameras 28 attached to the distal end of the robotic arm (proximate the end-effecter assembly 30). In alternate embodiments, only a single camera need be used for image acquisition. Also, as depicted in FIG. 2 (and also as described in greater detail herein), multiple pairs of stereo cameras 28A and 28B may be used in order to capture differing (i.e., broader and narrower) fields-of-view. In still further embodiments, a single camera may be used to capture a first (i.e., broad) field-of-view, and a second camera may be used to capture a second (i.e., narrow) field-of-view. Other camera configurations are also possible.

Image data acquired by the camera(s) 28 is processed in a computer (not shown in FIG. 1) associated with the robotics system 25, which provides control signals to the system controller for directing movement of the robotic arm 27. In particular, images are acquired from each camera of the pair 28 at a desired magnification (e.g., in a range of 6× to 10× in one embodiment) and duty cycle (e.g., 30 hertz in one embodiment). The acquired images are digitized using known image segmentation techniques implemented in software on the computer in order to identify the position(s) and orientation(s) of objects of interest. In the case of procedures involving the removal or implantation of hair follicles, it may be desirable to die the hair follicles of interest with a dark color prior to a procedure, in order to increase the effectiveness of the image processing techniques. It may also be desirable to cut the hair follicles in the region(s) of interest to a substantially uniform length prior to the procedure.

As will be appreciated by those skilled in the art, one can visualize below the skin surface by adjusting the lighting, filters on the cameras, and various image processing techniques. This is because the reflection and absorption of light by the skin surface will change based on the wavelength of light used. Further, the depth of penetration of the light itself into the skin also varies based on the wavelength. Understanding these basic properties of light, images of the subcutaneous portions of the follicular units (hair follicles) may be obtained using appropriate respective wavelengths of light, including both visible light spectrum and infrared, capturing the different wavelengths of light using different imaging filters, and subtracting and/or combining images during image processing. This approach enables one to visualize the hair shaft of the follicular unit, both outside the skin, as well as under the skin surface, including all the way down to the bulb.

More particularly, the robotics system 25 is able to precisely track movement of the distal end plate (and end-effecter tool or assembly) in each of the six degrees of freedom (x, y, z, co, p, r) relative to three different reference frames. A "world frame" has its x,y,z coordinate origin at a center point of the base 32 of the robotic arm 27, with the x-y coordinates extending along a plane in a surface of a table 36 on which the base 32 of the robotic arm 27 is attached. The z-axis of the world frame extends orthogonally to the table surface through a first section of the robotic arm 27. A "tool frame" has its x,y,z coordinate origin established at the distal end tool plate. Lastly, a "base frame" may be registered relative to the world and tool frames. Each camera also has a (two-dimensional) camera coordinate system ("camera frame"), in which the optical axis of the camera ("camera axis") passes through the origin of the x,y coordinates. By aligning the respective world frame, tool frame, base frame and camera frames, the system controller can precisely position and orient an object secured to the tool plate (e.g., a needle) relative to another object, such as a hair follicular unit extending out of a patient's skin surface.

Figure 4:
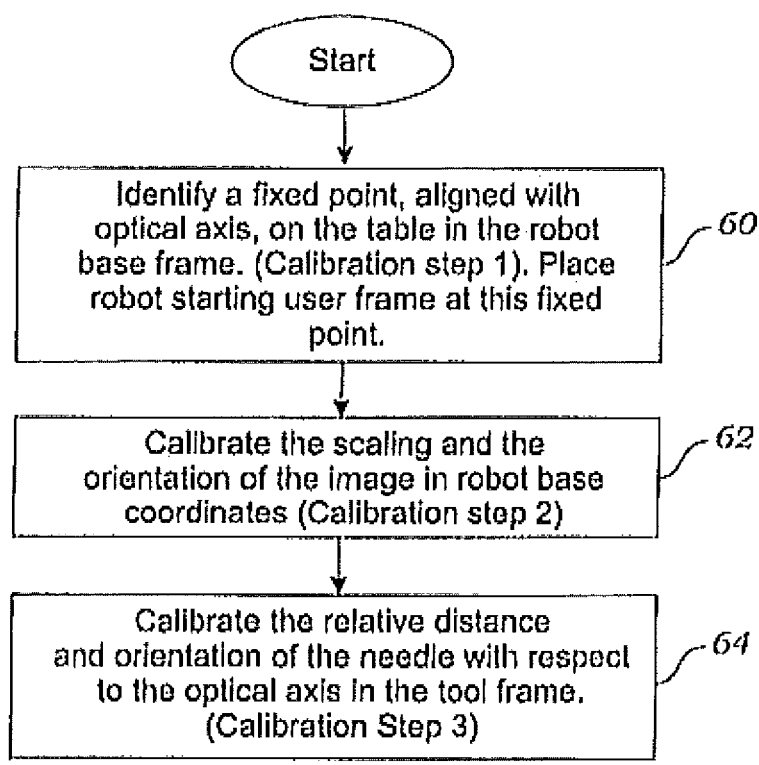
FIG. 4 is a flow diagram of a procedure for calibrating an optical axis and associated camera reference frame of a single camera with a tool frame established at the distal (working) end of the robotic arm to which the camera is attached.

In order to physically align the camera axis with an axis of an end-effecter tool (e.g., an elongate needle cannula) fixed to the distal tool plate of the robotic arm 25, it is of practical importance to be able to calibrate, and thereby have the information to compensate for, the positional and rotational offsets between the end effecter "tool axis" and the camera axis, as well as the deviation from parallel of these respective axes. An exemplary calibration procedure is illustrated in FIG. 4. As an initial matter, the proximal base of the robotic arm 27 is mounted to the table surface 36, so that the table surface 36 is aligned with the x-y coordinate plane of the world frame of the robotic system. Thus, a point lying anywhere on the table surface has a x-y coordinate location in the world frame, which can be identified in terms of x and y offset values (e.g., measured in mm) from the origin of the world frame located at a center point of the robotic arm proximal base interface with the table surface 36, with the z coordinate location of the point in the world frame equal to zero.

At step 60, the camera axis of a single camera fixed to the distal end tool plate of the robot arm 27 is aligned with a fixed "calibration point" located on the table surface 36. The base frame of the robotic system is then initiated, meaning that the origin of the base frame is set at the "calibration point" and the camera axis is aligned with the calibration point on the table surface. This initial position is called "home" position and orientation, and the robot arm 27 always starts from this position, even in the absence of the calibration point.

At step 62, a scaling and orientation of the camera image relative to the base frame is then determined by first moving the robotic arm 27 (and, thus, the camera) a fixed distance (e.g., 5 mm) along the x axis of the base frame, so that the calibration point is still captured in the resulting image, but is no longer aligned with the camera axis. Because the camera frame x-y axes are not aligned with the base frame x-y axes, movement along the x axis of the base frame results in movement in both the x and y directions in the camera frame, and the new location of the calibration point is measured in the camera frame as a number of image pixels in each of the x and y directions between the pixel containing the relocated camera axis and the pixel containing the calibration point.

This process is repeated by moving the robotic arm 27 (and camera) a fixed distance (e.g., 5 mm) along the y axis of the base frame, and again measuring the x,y offsets in the camera frame of the new location of the calibration point. As will be appreciated by those skilled in the art, these measurements allow for scaling the physical movement of the robot/camera (in mm) to movement of an object in the camera image (in pixels), as well as the in-plane orientation of the x-y axes of the camera frame relative to the x-y axes of the base frame. It will further be appreciated that the scaling and orientation process of steps 60 and 62 are repeated for each camera in a multiple camera system, whereby variances in image movement between respective cameras may also be determined and calibrated.

At step 64, once the camera frame is calibrated with respect to the base frame, the camera axis is again aligned with a fixed calibration point lying on the surface of table 36, wherein the base frame is returned to is "home" position and orientation (0,0,0,0,0,0). The robotic arm 27 is then moved in one or more of the six degrees of freedom (x, y, z, ω, ρ, r), so that an end effector tool (e.g., needle tip) attached to the tool plate contacts the calibration point. By precisely tracking the movement of the robotic arm 27 from the initial home position/orientation of the tool frame to its position/orientation when the tool tip is contacting the calibration point, the system controller calculates the translational and rotational offsets between the initial home position and the camera axis. Because the camera is fixed to the tool plate, the measured offsets will be constant, and are used throughout the procedure for alignment of the tool frame with the camera frame (and, by extension, the base frame).

As will be described in greater detail herein, when using a stereo pair of cameras, e.g., camera pair 28 in FIG. 1, the respective optical axes (and camera frames) of the cameras are typically not installed or maintained in parallel, but are slightly verged, e.g., about 10 degrees, which may be compensated for through known image processing techniques. In particular, the respective camera frames are aligned to have a common x (horizontal) axis, whereby a position and orientation (including in-plane depth) of objects captured in the parallel images may be aligned using image-processing techniques. One advantage of using a stereo camera pair 28 is that a "depth" in the camera frame of an identified object may be calculated based on the differences of the x,y position offsets of the object in the respective (left v. right) camera frames. In particular, the depth of implantation of a hair follicular unit ("graft") is important to the aesthetic result and is a challenge to achieve manually, particularly with the operator fatigue that results when a large number of grafts are implanted. If the graft is implanted too deep, a divot-like appearance results; if implanted too shallow, a bump results or the graft may not stay in position.

In order to calculate a depth of a selected object, such as a hair follicular unit, the left and right images obtained from the stereo camera pair must first be aligned. Because the respective camera images are aligned horizontally, the same objects will appear in the same horizontal scan lines of the two images. And, because the depth of an object being imaged relative to the camera lenses is within a known range (e.g., established by the focal lengths of the respective cameras), a selected object in a first image (e.g., a hair follicular unit) can be matched to itself in the second image (to thereby align the images with each other) by calculating an effective depth of the object when paired with the possible candidate objects in the second image (i.e., in the same scan line) to determine which "pair" has a calculated depth in the possible range.

Another advantage of using a stereo camera pair 28 is the ability to obtain image data regarding the position and orientation of an end-effecter tool (e.g., a hair follicular unit harvesting tool 40 shown in FIGS. 2 and 3) in a same reference frame that image data is obtained regarding the position and orientation of objects of interest (e.g., hair follicles, wrinkle lines, tattoos, moles, etc.) on the skin surface. The respective left and right camera frames are calibrated with the tool frame in the same manner as described above for a single camera frame. Once these offsets are established, the relative positions and orientations of the end-effecter tool and objects on the skin surface (e.g., hair follicular units) may be determined and tracked in the tool frame.

Figure 5:
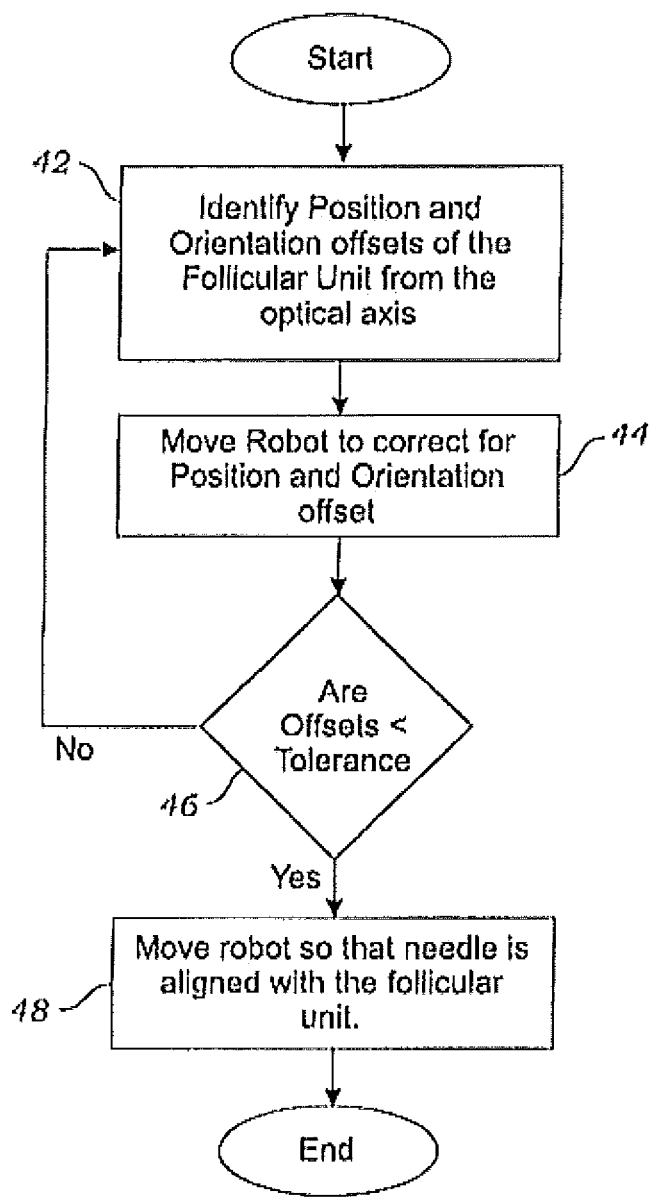
FIG. 5 is a flow diagram of an iterative procedure for aligning (both position and orientation) an elongate end-effecter tool used for harvesting and/or implanting hair follicles with a selected hair follicular unit.

FIG. 5 is a simplified flow diagram of a procedure according to one embodiment of the invention for aligning the position and orientation of an elongate axis of the follicular unit harvesting tool 40 with an elongate shaft axis of a hair follicular unit extending from the scalp, using only a single camera for image acquisition. Briefly, the harvesting tool 40 generally comprises a hollow, tubular cannula having a sharpened distal end for puncturing the epidermis and dermis immediately around an outer circumference of a follicular unit in order to envelop, capture and remove the entire follicular unit from the fatty subcutaneous tissues underlying the dermis, e.g., by rotating the cannula in a drill-like motion, or by a quick reciprocating thrust along its longitudinal axis. The harvesting tool 40 may be advanced and withdrawn by its own longitudinal motion (i.e., relative to the tool plate to which it is attached), or by longitudinal motion of the robotic arm 27, or by a combination of both, in order to core and remove the respective follicular units, e.g., by friction and/or with the aid of a weak vacuum. For example, the end-effecter may have its own controller and actuation system that is separate from the robotics system 25.

Figure 11:
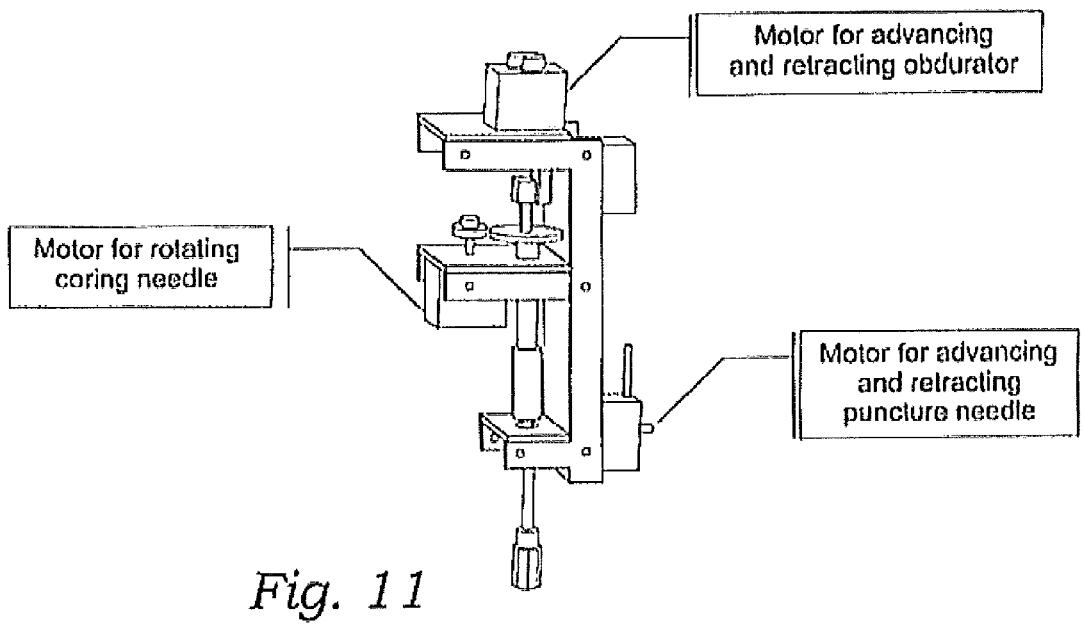
FIG. 11 is an end-effecter apparatus used for driving the respective three parts of the three-part tool of FIG. 10.
Figure 12:
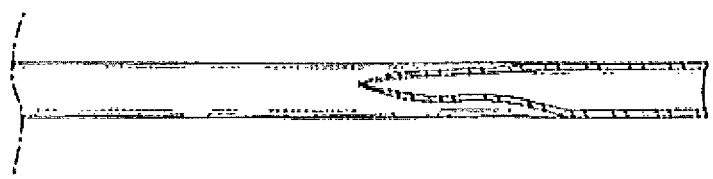
FIG. 12 is a photograph of a semi-circular cylinder used as a rotational cutter for harvesting hair follicles, according to one embodiment of the invention.

A more detailed description of exemplary follicular harvesting tools and assemblies is provided below in conjunction with FIGS. 10-12. It should also be appreciated that the positioning and orientation process used for aligning the elongate axis of the harvesting tool 40 with the elongate axis of a hair follicular unit will have much broader applicability than just for hair removal and/or implantation procedures. By way of non-limiting examples, substantially similar positioning and orientation procedures may be used for aligning a laser, or an injection needle, with desired physical features and/or locations on a patient's skin surface in a timely and precise manner.

Figure 7:
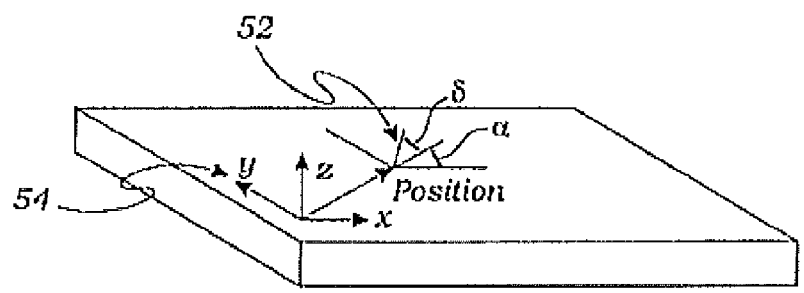
FIG. 7 illustrates exemplary position and orientation, i.e. defined by x,y offsets and in-plane and out-of-plane angles, of a hair follicular unit relative to the camera reference frame.
Figure 6:
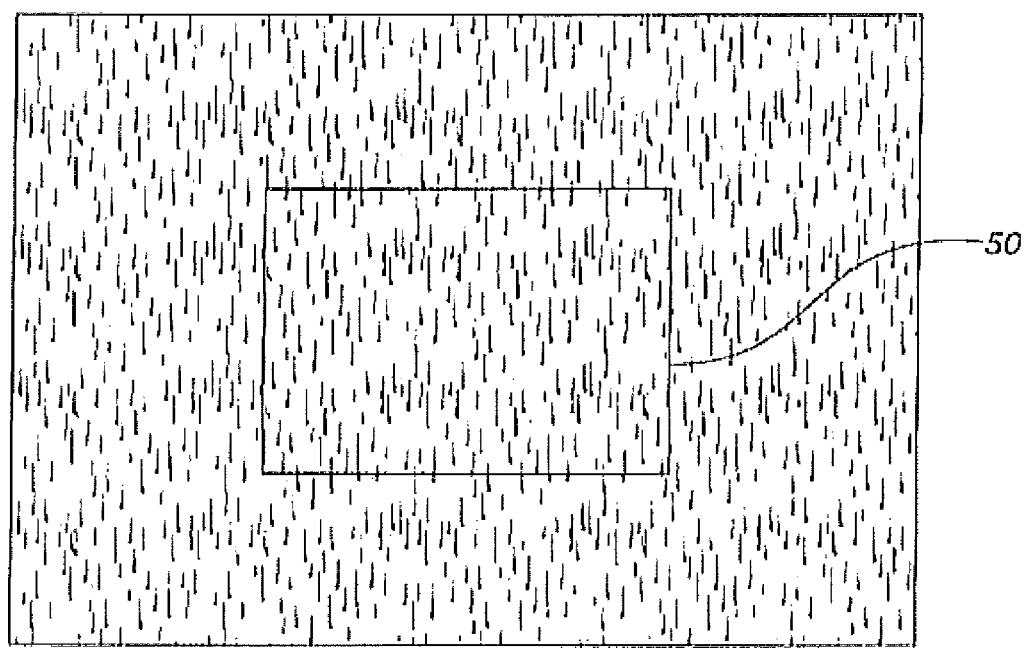
FIG. 6 depicts a camera image of hair follicular units in a region of interest on a human scalp.

After the robotics system 25 has been initiated and calibrated so that the camera frame is aligned with the tool frame (described above in conjunction with FIG. 4), image data is acquired and processed by the system computer to identify objects of interest in the camera frame. By way of example, FIG. 6 depicts, a camera image of hair follicular units in a region of interest 50 on a human scalp. From images of this region of interest 50, image segmentation and screening software residing in the computer identifies and selects one or more particular follicular units of interest for harvesting from the scalp. With reference to FIG. 7, a position of a selected hair follicular unit 52 is identified in terms of its x,y offset coordinates in the camera frame (the z axis being the camera optical axis which is preferably aligned substantially orthogonal to the surface of the scalp at the region 50).

Unless the camera axis happens to be exactly aligned with the longitudinal axis of the follicular unit 52 (in which case the follicular unit will appear as a circular point representing an end view of the hair shaft), the image of follicular unit will be in the form of an elongate line having an "apparent" length that will depend on the angle of the camera frame relative to the follicular unit. Because of physical attributes of a hair follicular unit, its base (i.e., the end emerging from the dermis) can be readily distinguished from its tip as part of the image segmentation process. For example, the base portion has a different profile and is generally thicker than the distal tip portion. Also, a shadow of the follicular unit can typically be identified which, by definition, is "attached" at the base.

The x,y locations of the follicular unit base in the camera frame are then calculated and represent the position offsets of the hair base. Orientation offsets of the follicular unit 52 are also calculated in terms of (i) an in-plane angle $\alpha$ formed by the identified follicular unit shaft relative to, and in the same plane as, the x (or y) axis of the camera frame; and (ii) an out-of-plane angle $\delta$ that is an "apparent" angle formed between the follicular unit shaft and the scalp, i.e., between the follicular unit and the plane of the x,y axes of the camera frame. As noted above, the hair shaft is preferably trimmed prior to the procedure to a substantially known length, e.g., 2 mm, so the out-of-plane angle $\delta$ may be calculated based on a ratio of a measured apparent length of the image of the follicular unit to its presumed actual length, which ratio is equal to the cosine of the out-of-plane angle $\delta$.

Returning to FIG. 5, at step 42, the x,y position and orientation offsets are identified for a selected hair follicular unit, as described above. The computer then calculates the necessary movements of the robotic arm 27 to cause the camera axis to be aligned in the same position and orientation of the calculated offsets. The base frame and tool frame are also "moved" by the same x,y and rotational offsets (i.e., until angles $\alpha$ and $\delta$ are both equal to 0), so that the camera, base and tool frames remain aligned at the new position and orientation of the camera axis. Because of the inherent possible variances and errors in the system and in the assumptions (e.g., regarding the hair follicular unit length) the actual position and orientation of the hair follicular unit may not match the calculated values. Thus, once the robotic arm 27 (and camera axis) is moved by the calculated positional and rotational offsets, the follicular unit is again imaged and (at step 46) a determination is made as to whether the camera axis is aligned with the position and orientation of the follicular unit within acceptable tolerances. If the camera axis is adequately aligned with the follicular unit, the robotic arm 27 is moved a last time (at step 48) in order to align the harvesting tool 40 in the "confirmed" position of the camera axis (i.e., based on the offsets obtained in the above-described calibration process). However, if the (in step 46) the camera axis is not adequately aligned with the hair follicular unit, the procedures in steps 42-46 are repeated, starting from the new camera axis location.

As will be appreciated by those skilled in the art, in embodiments of the invention, the duty cycle of the image acquisition and processing is substantially faster than the movement of the robotic arm 27, and the process of identifying and calculating position and orientation offsets of selected hair follicular units relative to the camera axis can effectively be done "on-the-fly," as the robotic arm is moving. Thus, the end destination (i.e., position and orientation) of the robotic arm 27 (and harvesting tool 40) may (optionally) be constantly adjusted (i.e., fine tuned) as the harvesting tool 40 is moved into alignment with the follicular unit. Because such adjustments begin immediately, movement of the robotic arm 27 is more fluid and less jerky. This iterative feedback process, referred to as "visual-servoing," continually calculates and refines the desired position and orientation of the harvesting tool 40, in order to minimize the image of the hair follicular unit, i.e., until the image transforms from a line to a point.

Thus, in embodiments of the invention, the image-guided robotics system 25 may be used to perform automated or semi-automated procedures for identifying position and orientation of a large number of hair follicular units in a region of interest on a patients scalp, and then accurately harvest some or all of the follicular units. One or more cameras attached to the working distal end of the robotic arm capture images at a desired magnification of a selected area of the patient's scalp. A computer system processes the images and identifies (through known thresholding and segmentation techniques) the individual hair follicular units, as well as their respective positions and orientations relative to the camera frame. Through a user-interface (e.g., a display and a standard computer mouse), an attending surgeon may define a region on the scalp from which hair follicular units are to be harvested and defines a harvesting pattern, such as, e.g., taking every other hair follicular unit in the region, leaving a defined number of follicular units between harvested follicular units, taking a certain percentage of follicular units, leaving behind an aesthetically acceptable pattern, etc.

For example, images obtained from a wide field-of-view pair of stereo cameras may be used by the attending physician to locate generally a region of interest, while images obtained from a narrow field-of-view pair of stereo cameras are used to accurately guide the harvesting tool with the individual selected follicular units. Once the hair follicular units to be harvested have been identified, the robotics system systematically aligns a harvesting tool (e.g., harvesting tool 40) with each hair to be harvested; the respective hair follicles are harvested, and the process is repeated for all of the selected follicular units in the defined harvest region. It will be appreciated that in some cases, the individual hair follicular units being harvested are then implanted in another portion of the patient's scalp, whereas in other instances the harvested hair follicular units are discarded. It will also be appreciated that, rather than a coring harvesting tool, such as tool 40, another type of hair removal end-effecter tool may be employed, such as, e.g., a laser. It will be still further appreciated that the above-described techniques for aligning the camera frame with the robot tool frame for precisely aligning an end-effecter tool may be equally applicable to other types of end-effecter tools, such as an injection needle (or a plurality of injection needles) used for injecting ink for forming tattoos on a skin surface of a patient.

Figure 8:
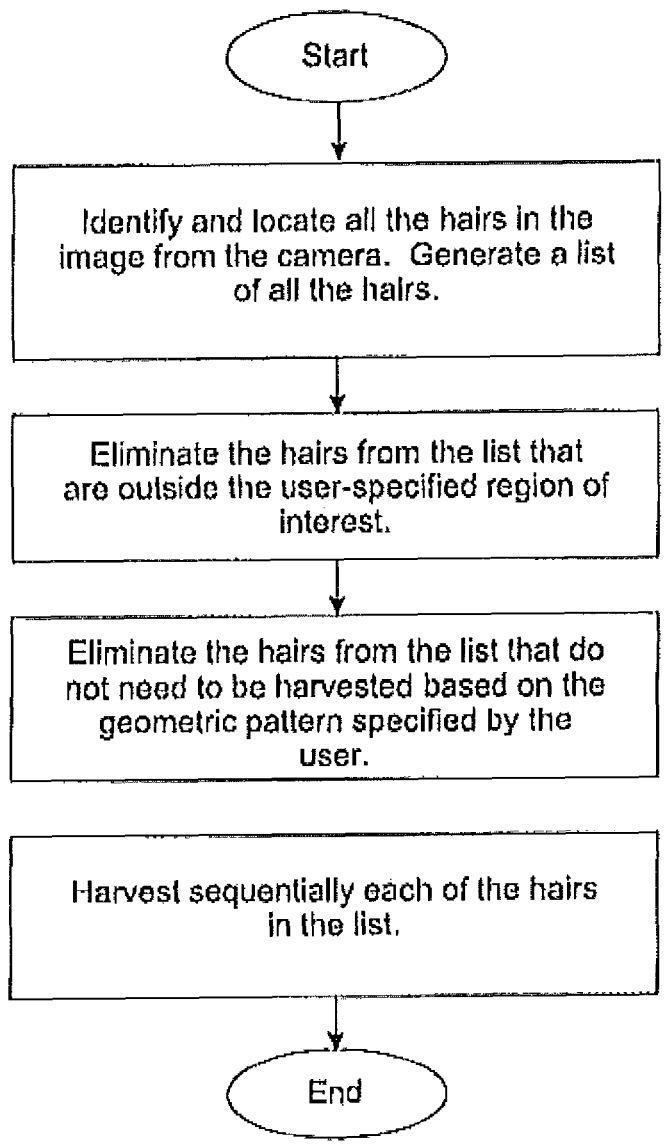
FIG. 8 is a flow diagram of an automated procedure for identifying a position and orientation of each of a multiplicity of follicular units in a region of interest on a human scalp, and then harvesting some or all of the identified follicular units.

FIG. 8 is a flow diagram of an automated (or semi-automated) procedure for identifying a position and orientation of all follicular units in a region of interest on a patient's scalp, and then accurately harvesting some or all of the identified follicular units.

Figure 9:
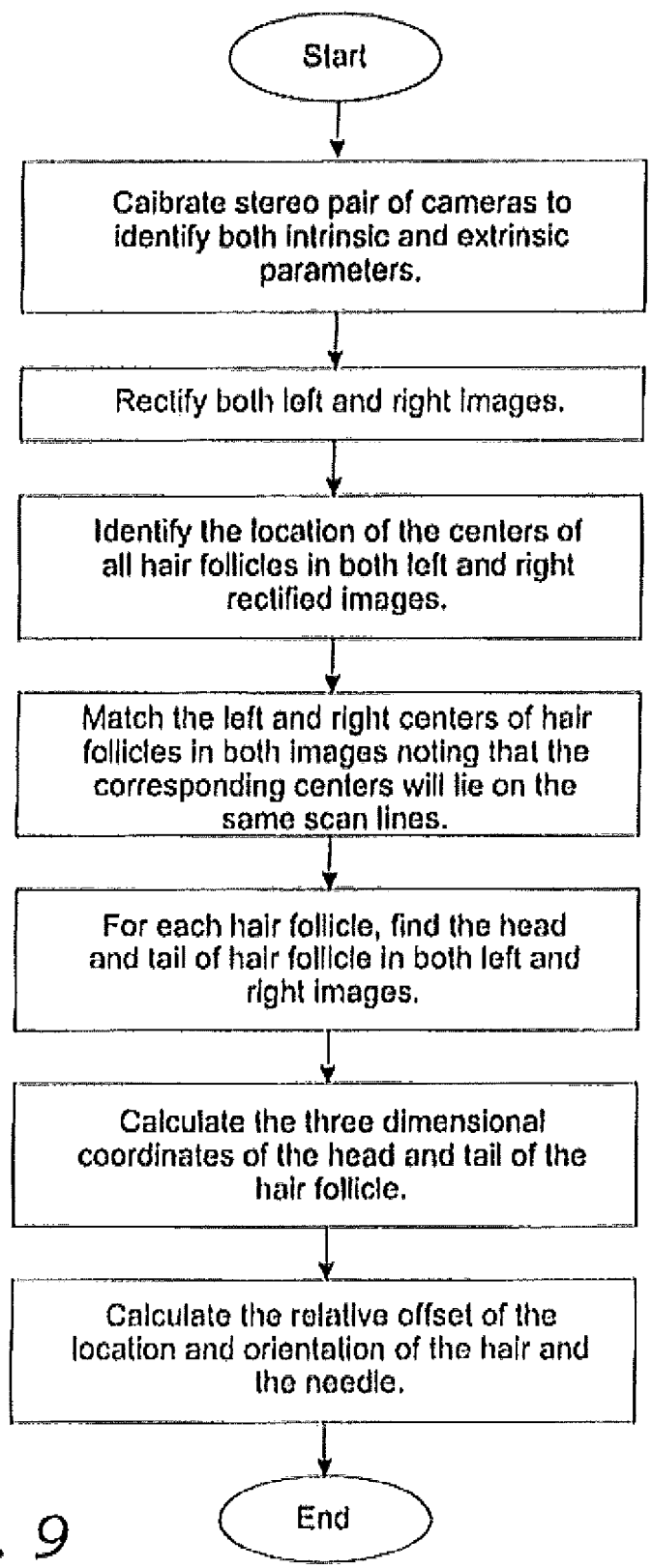
FIG. 9 is a flow diagram of an algorithm that uses images acquired from a stereo pair of cameras for identifying follicular units in a region of interest, and then computes the respective locations and orientations of the identified follicular units.

FIG. 9 is a flow diagram of a procedure using a stereo pair of cameras to identify individual follicular units in a region of interest on a patient's scalp, and then compute a location and orientation of each in the respective camera frames and robot tool frame. The procedure starts by calibrating the stereo pair of cameras to identify both intrinsic and extrinsic parameters, in accordance with well known techniques. Intrinsic parameters are intrinsic to the individual camera, such as internal optics, distortion, scaling, and the like. Extrinsic parameters relate to characteristics between the two cameras, e.g., differences in the alignment of their respective optical axes (which are ideally parallel to one another, but as since this is unlikely as a practical matter, mathematical compensation is required). Calibration of intrinsic and extrinsic parameters are known in the field of stereo imaging and will not be explained in detail herein. As discussed above, the locations of the centers of the hair follicles are identified and matched in both the left and right rectified images. The head and tail of each hair follicle is then identified in both the left and right images, wherein the three dimensional coordinates of the head and tail of the hair follicle may be calculated. Finally, the relative offset of the location and orientation of the hair follicle and the cannula are determined by employing the images of the cameras which see both the cannula and the hair follicle, in accordance with well known stereo imaging techniques.

The aesthetic result of a hair transplant procedure depends in part on implanting the grafts in natural-looking patterns. The computer can efficiently "amplify" the surgeon's skill by "filling in the blanks" among a small fraction of the implant sites for which the surgeon determines graft location and orientation. Achieving a natural-looking hairline is particularly important for a good aesthetic result. Instead of painstakingly making incisions for all of the near-hairline implant sites, the surgeon indicates a few hairline implant locations and orientations and the computer fills in the rest by interpolating among the designated sites, using the imaging system to identify and avoid existing follicular units.

Figure 13:
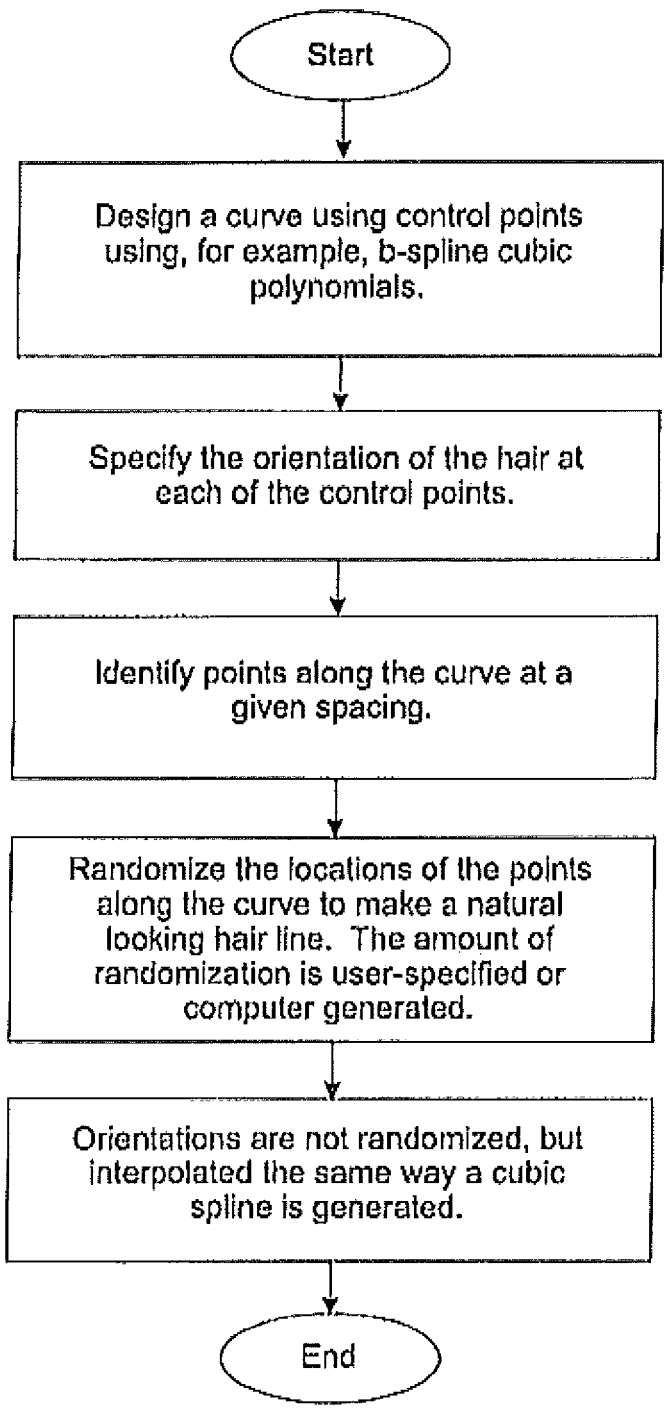
FIG. 13 is a flow diagram of an algorithm using control points to design a natural looking (implanted) hairline.

FIG. 13 illustrates an algorithm using control points to design natural looking hairline. A curve is designed using control points based on, for example, b-spline cubic polynomials. The control points are specified by the operator. The orientation of the hair at each of the control points is specified. Points along the curve are identified at a given spacing, for instance, by interpolation. The locations of the points along the curve may be randomized to make a natural looking hair line. The amount of randomization may be user-specified or computer-generated. It is preferable that the follicular unit orientations are not randomized but are interpolated, for example, the same way a cubic spline is generated. Randomization of the location and interpolation of the orientation create more natural looking implants.

Figure 14:
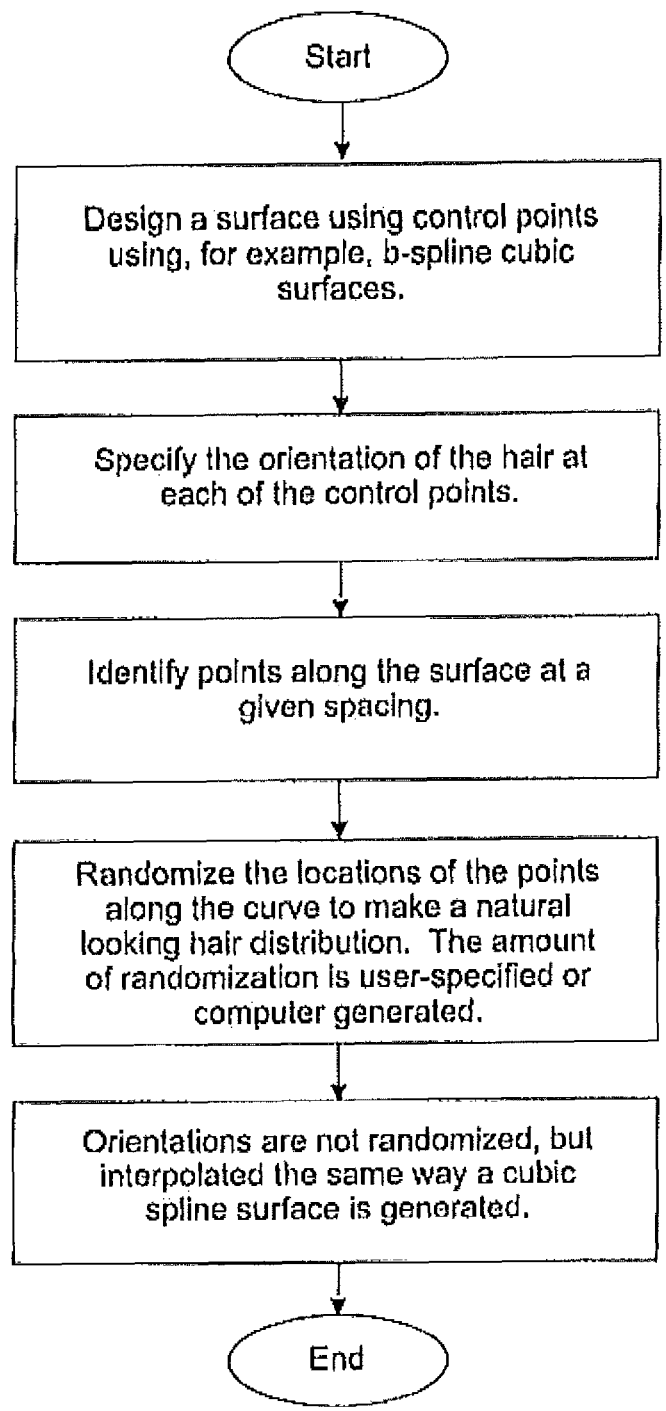
FIG. 14 is a flow diagram of an algorithm using control points to provide natural-looking randomness to implanted hair graft locations.

Natural looking randomness is important in both the critical hairline region and in the balance of the recipient sites. This can be achieved using the procedure illustrated in FIG. 14, wherein a surface is designed using control points based on, for example, b-spline cubic surfaces. Again, the orientation of the hair at each of the control points is specified. Implant points along the surface are identified at a given spacing. The locations of the points along the surface may be randomized to make a natural looking hair distribution. The amount of randomization may be user-specified or computer-generated. Again, the orientation of the respective follicular units is preferably not randomized, but interpolated the same way a cubic spline surface is generated. Randomization and interpolation schemes are known in the art, and can be adapted for this method.

It is often desirable to leave the existing hair in the recipient region at its natural length, which can interfere with the vision system's access to individual recipient sites. This can be overcome by a gentle air jet directed at the recipient site, causing the hair in that region to be directed away from the target site. If necessary, the hair can be dampened to facilitate this step. The air jet also can disperse blood that emerges from the incised recipient site, thus maintaining visual access during graft implantation. Such an air jet can be part of a more complex end-effecter assembly attached to the robotic arm tool plate, and which may also include one or more hair follicle harvesting and/or implantation needles.

Figure 15:
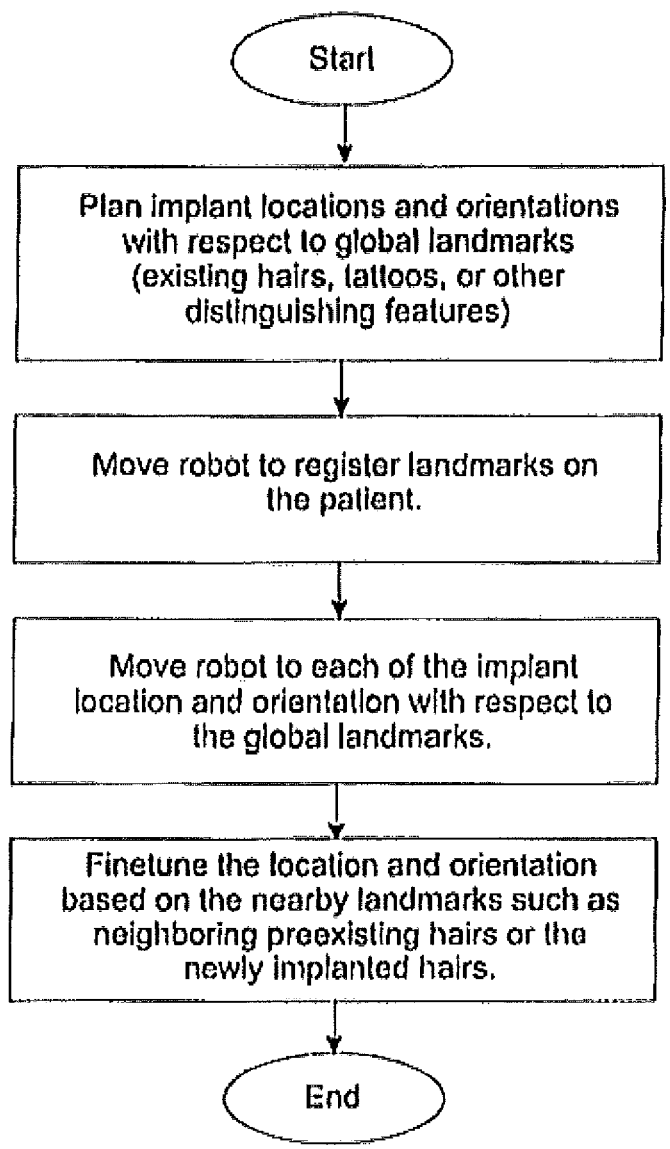
FIG. 15 is a flow diagram illustrating an automatic guidance feature of an image-guided robotics system.

The robotics system 25 uses real-time information from the vision system to monitor the position of the patient (typically using fiducial markers in the recipient region of the scalp), of the implanting tool, and of existing follicular units to guide the implanting tool into place for incising the recipient site and implanting the graft. FIG. 15 shows an example of the automatic guidance feature of the robotic system, including the step of planning implant locations and orientations with respect to global landmarks (e.g., existing hairs, tattoos, or other distinguishing features). The robot is then moved to register landmarks on the patient. The register information can be stored in memory for reference. The robot can make use of the registered landmarks as reference points for recognizing its position relative to the working surface. The robot is moved to each of the implant location and orientation with respect to the global landmarks. The global landmarks provide a global reference for global movements. The location and orientation are fine-tuned based on the nearby landmarks such as neighboring preexisting hairs or newly implanted hairs. The nearby landmarks provide a local reference for local movements.

Hair transplantation generally includes three steps: follicular unit harvesting, recipient site incision, and graft placement. The efficiency of the surgery can be enhanced if these functions are accomplished with a single tool. FIG. 10 shows an embodiment of a three-part tool for accomplishing the three functions. The three coaxial elements are an outer cannula ("puncture needle") with a sharp bevel cut that is used for making the recipient-site incision, a second cannula ("coring needle"), that slides inside the outer needle and is used for cutting around the donor graft, and an obdurator that slides inside the second cannula and is used for positioning the graft at the appropriate depth in the recipient site. For harvesting, the second cannula cuts the tissue (by rotating or by a quick thrust) while being advanced to the desired depth for separating the follicular unit from the skin down to the level of fatty tissue. The graft is then captured within this cannula by advancing the cannula into the fatty tissue surrounding the follicular unit bulb without a cutting motion. The cannula then extracts the graft using friction between the graft and the inside of the cannula or a combination of such friction and vacuum. For recipient site incision, the outer cannula is advanced beyond the harvesting cannula and is use to make an incision at the desired location with the desired orientation and depth. The obdurator then holds the graft at the desired depth while the two cannulae are retracted.

Figure 10:
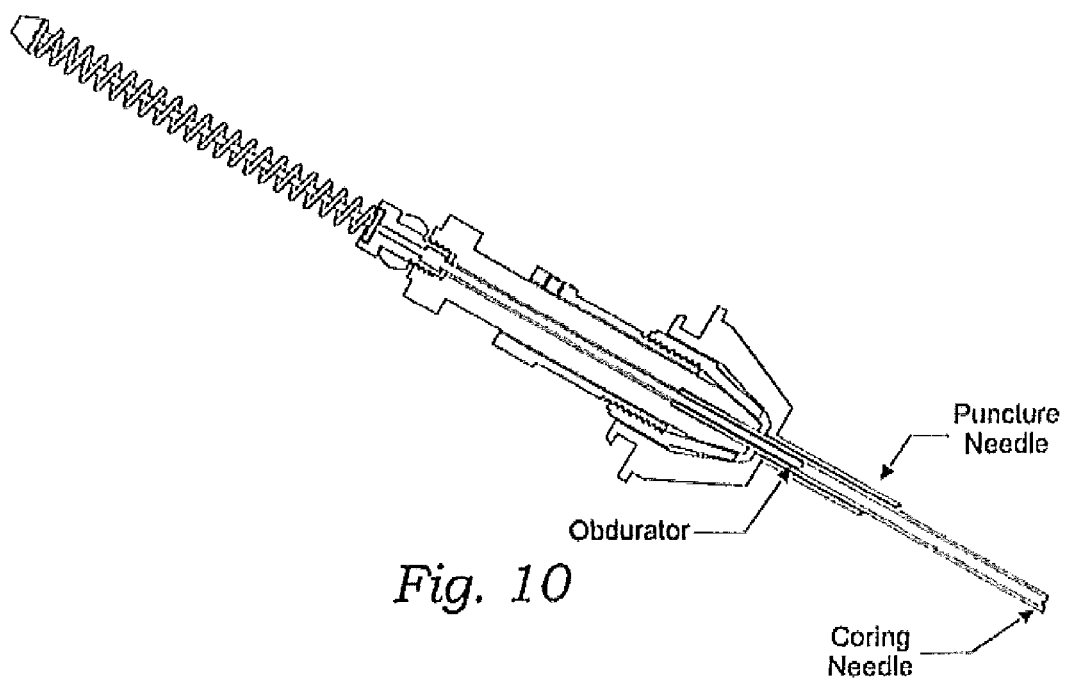
FIG. 10 is a three-part tool for follicular unit harvesting, recipient site incision, and graft placement, according to one embodiment of the invention.

In the three-part tool of FIG. 10, it is necessary to move each of the three elements independently of the other two. And, if the harvesting cannula cuts by rotation rather than a linear quick thrust, there is a mechanism for rotating that cannula. FIG. 11 shows an embodiment of an apparatus for producing the required motions of the tool elements, including rotation and advancement of the harvesting cannula, advancement and retraction of the implant cannula, and advancement and retraction of the obdurator. A translation mechanism or linear motor provides advancement and retraction of the implant cannula. A rotation and advancement motor or mechanism provides both translational and rotational movement of the harvesting cannula. Another translation mechanism or linear motor provides advancement and retraction of the obdurator. The mechanisms and motors typically employ a combination of motors, cams, and springs, but any suitable mechanism can be used to provide translational and rotational movement of the tool parts.

Figure 17:
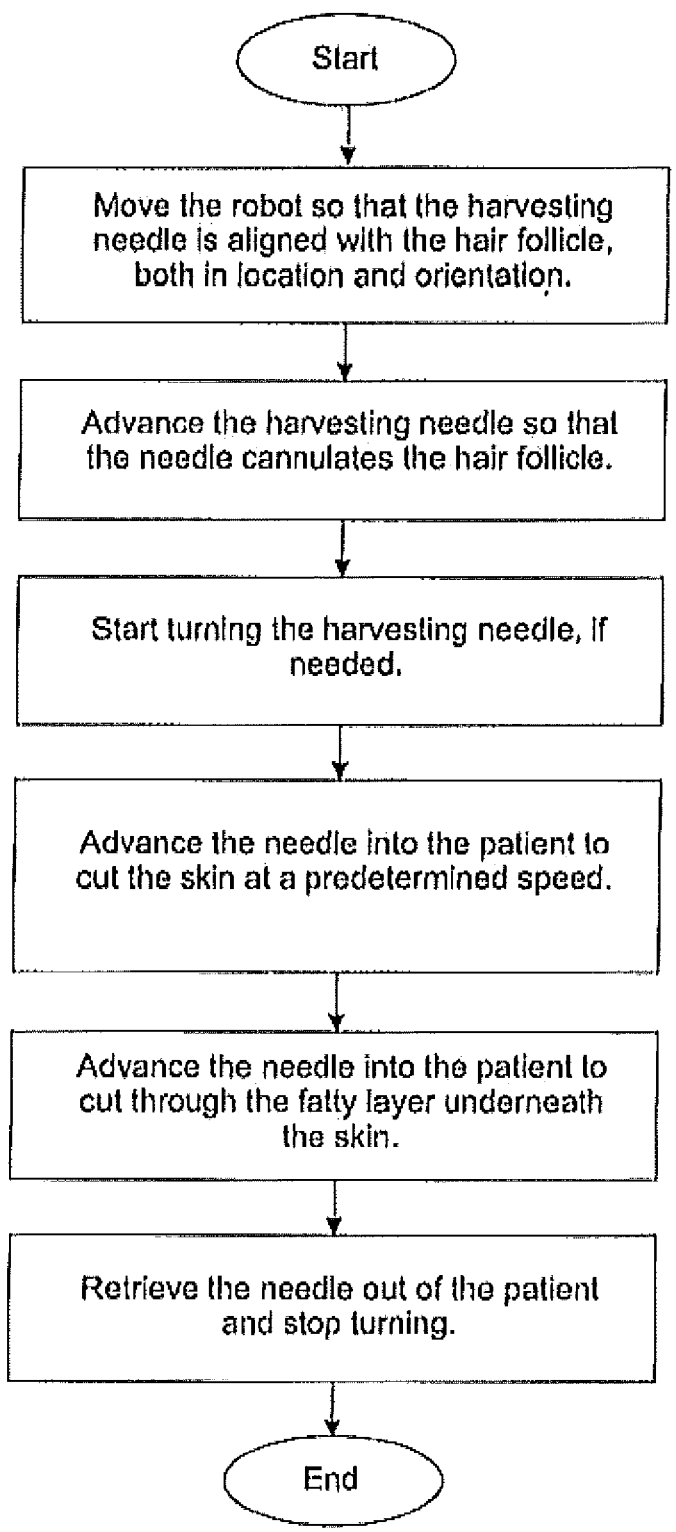
FIG. 17 is a flow diagram of a procedure for harvesting hair follicles.

FIG. 17 depicts a general sequence of actions for harvesting hair follicles using a system according to embodiments of the invention, Initially, the robot is moved so that the harvesting needle is aligned with the hair follicle, both in location and orientation. The harvesting needle is then advanced so that the needle cannulates the hair follicle. The needle is advanced into the patient to cut the skin at a predetermined speed in step (e.g., to produce a quick jab or thrust). The needle is advanced into the patient's scalp to cut through the fatty layer underneath the skin. The needle is retrieved out of the patient and stops turning. Sometimes, the hair follicle will be lifted by the harvesting needle, as the harvesting needle is retrieved. Alternatively, an extraction mechanism, such as a vacuum, can be provided to extract or harvest the hair follicle. The vacuum is coupled via a suction tube to the harvesting needle to provide suction to harvest the hair follicle.

Figure 16:
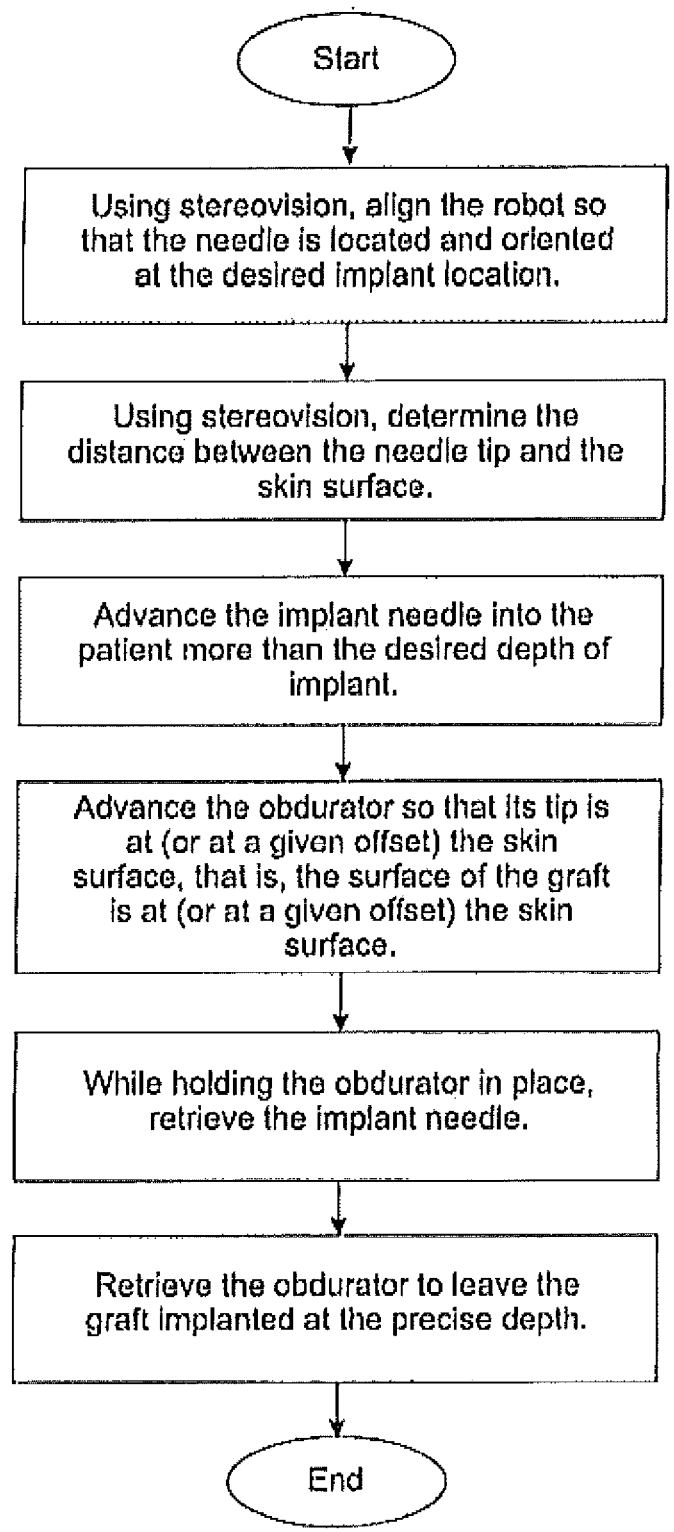
FIG. 16 is a flow diagram of an algorithm using stereo-vision for accurately controlling the depth of a hair follicle implant.
Figure 18:
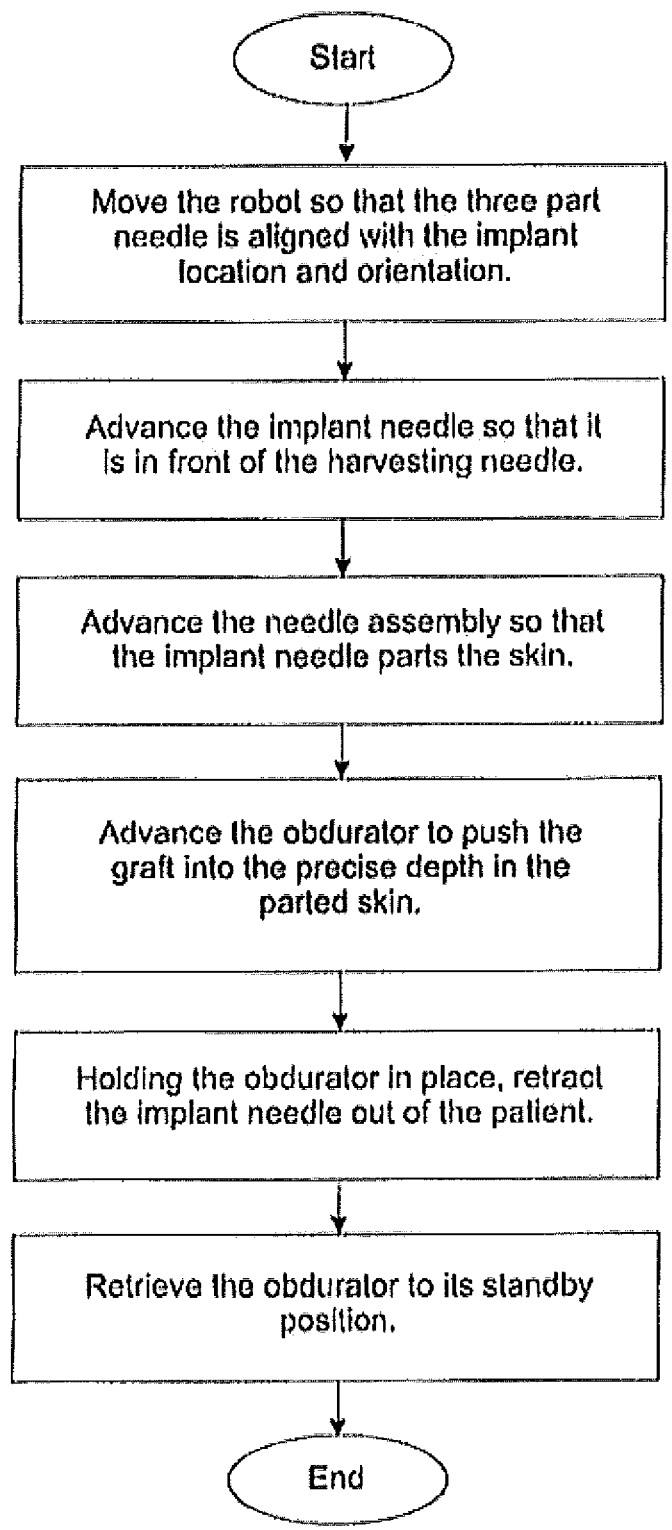
FIG. 18 is a flow diagram of a procedure for implanting hair follicles.

FIG. 18 depicts a general sequence of actions for implanting hair follicles using a system according to embodiments of the invention. Initially, the robot is moved so that the three part tool is aligned with the implant location and orientation. The implant needle is then advanced so that it is in front of the harvesting needle. The needle assembly or tool is advanced so that the implant needle parts the skin at the implant location. The obdurator is then advanced to push the graft into the precise depth in the parted skin. Holding the obdurator in place, the implant needle is then retracted out of the patient. The obdurator is then retrieved to its standby position. FIG. 16 is a flow diagram of a sequence of actions for accurately controlling the depth of the implant.

Another feature of the invention relates to the automatic loading and unloading of multiple needles and multiple-needle cassettes. In the typical procedure, the patient is prone or semi-prone during the harvesting of grafts from a donor region in the back of the head and is sitting erect during implantation of grafts in a recipient region at the front hairline or top of the head. While it is possible to harvest a single follicular unit from the donor site and then implant it immediately in the recipient site by suitably moving the robotic arm and/or the patient, it is faster to keep the patient in the prone or near-prone position while harvesting a number of grafts (hundreds, at least), then move the patient to the upright position for implanting all those grafts. This can be accomplished using cassettes that hold a number of tools, typically in the range of fifty to one hundred. The cassettes may be in the form of revolving cylinders with multiple chambers, one for each tool, or may have a rectilinear array of chambers. The individual tools are indexed into place for use in harvesting and implanting. Multiple cassettes may be sequentially loaded onto the robotic arm (an operation that can be either manual or automated using standard robot-loading procedures) to harvest and implant large numbers of grafts without changing the patient's position; for example, ten cassettes of one hundred chambers each would be used for one thousand grafts. It is possible to have just harvesting cannulae in the cassettes, using a single implanting cannula and obdurator for a number of harvesting cannulae by appropriately indexing the cassettes during the implanting stage of the transplant procedure.

For example, a cassette may have a plurality of chambers, and multiple cassettes can be provided in the robotic arm. While a circular cylindrical cylinder with a sharp cutting edge (which may be serrated to facilitate cutting) is an obvious configuration because of its similarity to dermatological biopsy punches, other shapes also work. For example, a semi-circular cylinder (as shown in FIG. 12) is an effective rotational cutter. If it is close to 360 degrees, it can capture the graft for extraction. If it is significantly less than 360 degrees, an additional cannula (which may be the implanting cannula) will be advanced to capture the graft. Similarly, an array of pins can be used for rotational cutting. Furthermore, shapes other than circular or semi-circular can be used for quick-thrust cutting.

In accordance with another aspect of the inventions disclosed herein, the robotic system 25 may be employed to perform procedures that involve the patterned removal of tissue. In particular, persons seek a "face lift" procedure because their skin has lost its elasticity and texture, and has stretched out. The surgeon's objective in performing a face lift is to restore texture and consistency, and to remove excess tissue. An undesirable side effect is that, when the surgeon pulls the tissue to tighten it, an unnatural rearrangement of anatomical features can result. For example, one well known technique is for the surgeon to remove an entire section of scalp, and pull the remaining scalp together to tighten the tissue. As an alternative to such wholesale tissue removal, it may be desirable to perform multiple (e.g., hundreds, even thousands) of "punch-biopsy" type micro-tissue removals in a predetermined pattern across a patient's scalp using an appropriately sized coring needle, and depend on the skin's natural ability to heal the micro-incisions, as it does following a hair transplantation procedure. An appropriate end-effecter needle would be used similar to the one used for harvesting hair follicles, but with a smaller coring diameter. Rather than targeting hair follicles, the same image processing techniques described above can be used to avoid harm to existing hair follicles, while removing bits of tissue throughout a targeted region of the scalp. By employing a relatively small needle, the wound healing process can occur without a resulting scar from an incision, and without the unnatural realignment of anatomical features. Use of the robotically controlled system for needle location, alignment and depth control allows for such a procedure within a relatively reasonable amount of time, and without the necessary complications and risks due to physician fatigue caused by repetitive manual tissue punches.

In accordance with yet another aspect of the inventions disclosed herein, the above-described image processing techniques and embodiments may be employed for diagnostic procedures with or without the robotic system. For example, the robotic arm 27 may be used to maneuver one or more cameras 28 fixed to the distal tool plate, but without any further end-effecter assembly. In the alternative, the one or more cameras may be mounted to a non robotic assembly, whether positionable or rigid, and whether stationary or movable. Or the one or more cameras may be hand held. By way of non-limiting examples, such procedures may include: (i) examination of a patient's skin surface, or below the skin surface; (ii) detection and/or monitoring and/or tracking changes in skin conditions over time; and (iii) for image data acquisition for supporting medical therapies such as the use of lasers, drug delivery devices, etc. Image data acquired by the imaging system can be stored as part of a patient's medical history. Also, image data acquired by the imaging system can be stored, later processed, and/or enhanced for use in a telemedicine system.

Figure 19:
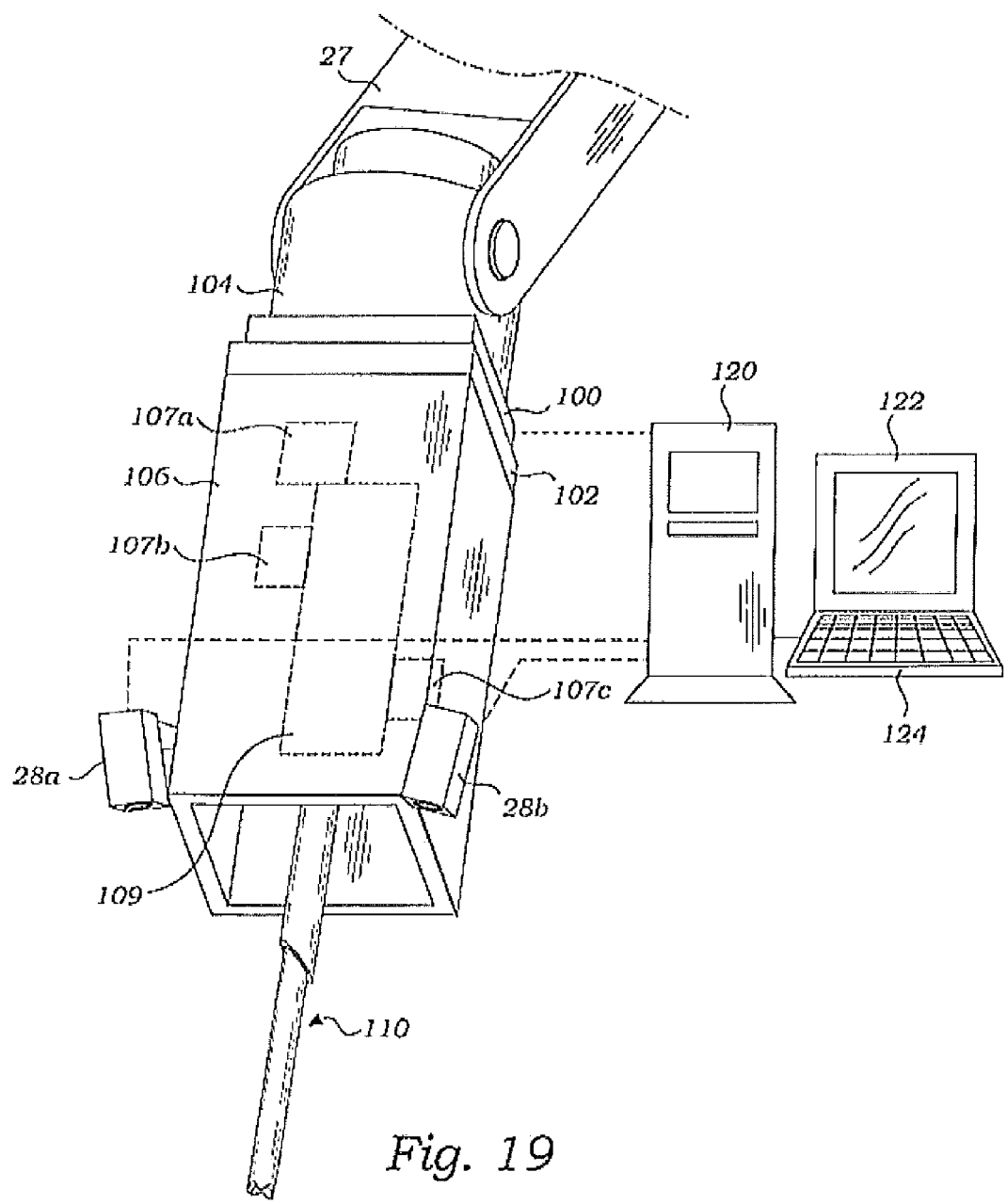
FIG. 19 illustrates an end-effector tool having a positioning assembly in accordance with some embodiments.

FIG. 19 illustrates a distal portion of the robotics system 25 in accordance with some embodiments. The robotics system 25 includes a force sensor 100 secured to an arm 104, a plate 102 mounted to the force sensor 100, and a positioning assembly 106 secured to the plate 102. Alternatively, the plate 102 could be secured directly to the arm 104, in which cases, the force sensor 100 may be secured between the positioning assembly 106 and the plate 102. In further embodiments, the force sensor 100 may be located within the positioning assembly 106.

The force sensor 100 is configured to sense three forces Fx, Fy, Fz in three different orthorgonal directions X, Y, Z, and three orthorgonal moments Mx, My, Mz. In other embodiments, the force sensor 100 may be configured to sense one or two of the forces Fx, Fy, Fz, and/or one or two of the moments Mx, My, Mz. As shown in the figure, the force sensor 100 is coupled to a computer 120, which receives data from the force sensor 100 representing the sensed force(s) and/or moment(s). In other embodiments, the force sensor data may go directly to the robot.

In the illustrated embodiments, the positioning assembly 106 includes a holding unit 109 for engagement with a needle assembly 110, and a plurality fo positioners 107a-107c. The holding unit 109 is configured to engage with different parts of the needle assembly 110 so that the needle assembly 110, as a whole, can be positioned by the positioning assembly 106. The holding unit 109 also allows different components of the needle assembly 110 to be controlled after the needle assembly 110 is engaged with the holding unit 109. The positioners 107a-107c are configured for moving different components of the needle assembly 110 after it has been engaged with the holding unit. Although three positioners 107a-107c are shown, in other embodiments, the positioning assembly 106 may include more or less than three positioners 107. In some embodiments, the positioning assembly 106 includes the device of FIG. 11, which includes three motors (positioners) for moving different components of the needle assembly 110.

Figure 20:
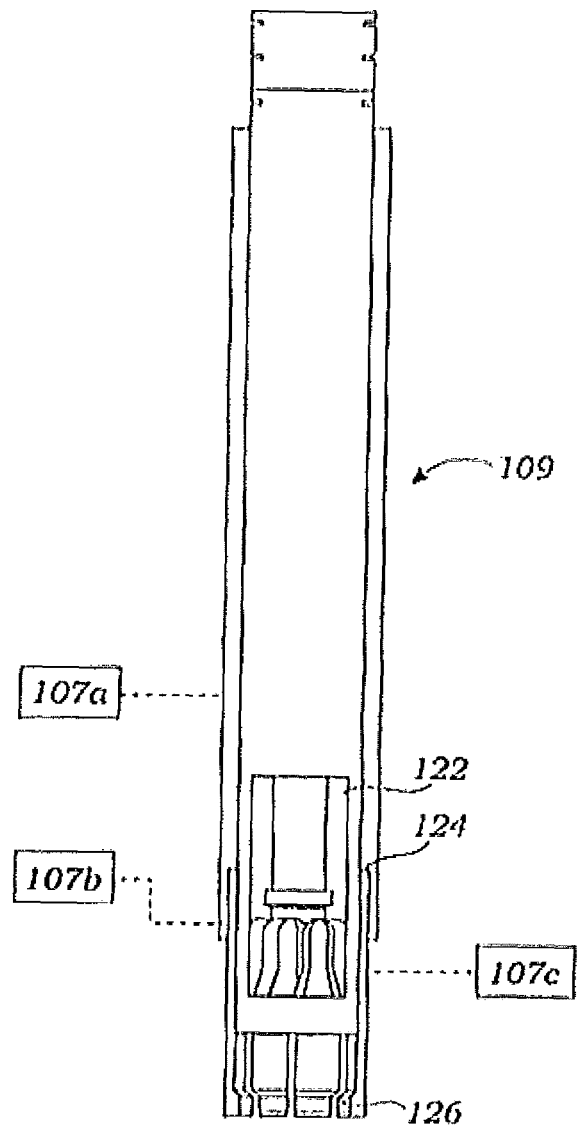
FIG. 20 illustrates a holding unit located within the positioning assembly of FIG. 19 in accordance with some embodiments.

FIG. 20 illustrates the holding unit 109 in accordance with some embodiments. The holding unit 109 includes a first engagement portion 122 for engaging a first portion of the needle assembly 110, a second engagement portion 124 for engaging a second portion of the needle assembly 110, and a third engagement portion 126 for engaging a third portion of the needle assembly 110.

Figure 21A:
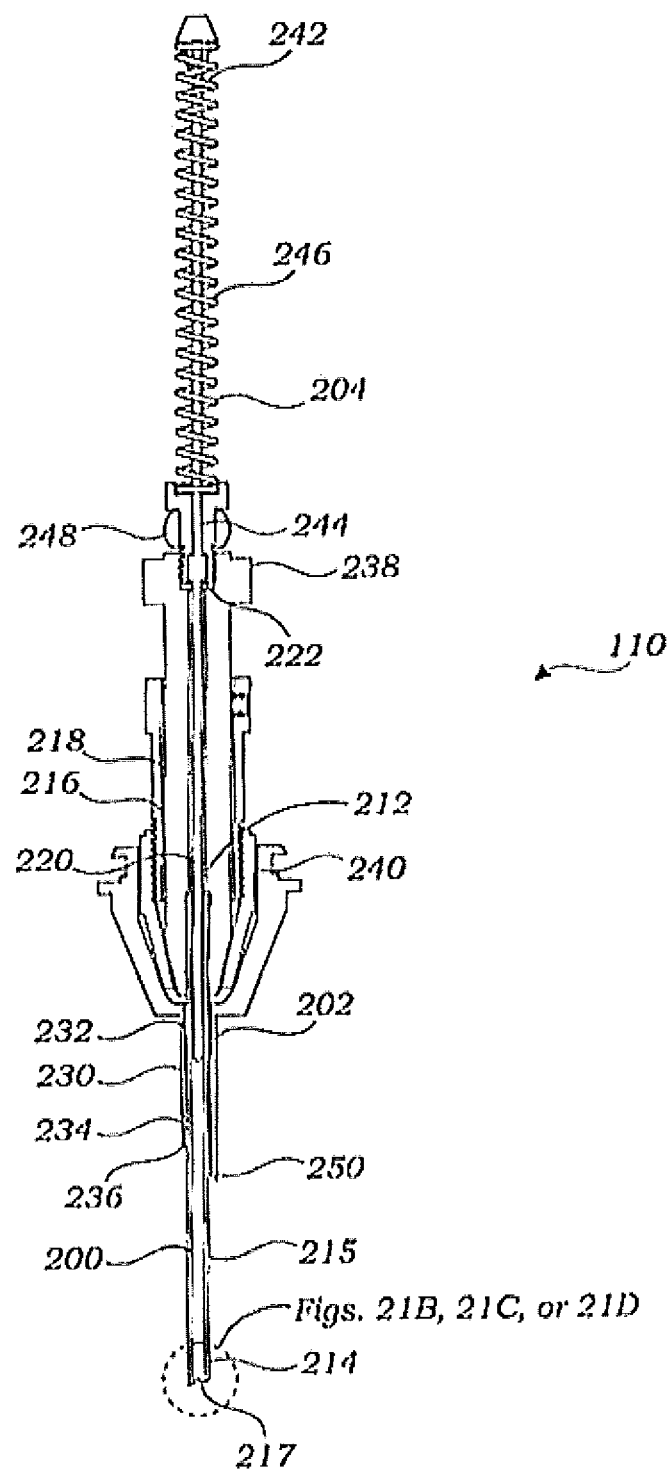
FIG. 21A illustrates a needle assembly in accordance with some embodiments.

FIG. 21A illustrates the needle assembly 110 in accordance with some embodiments. The needle assembly 110 has a similar configuration as that shown in FIG. 10. The needle assembly 110 includes a coring needle 200, a puncture needle 202, and a plunger (obdurator) 204. The coring needle 200 has a proximal end 212, a distal end 214, a body 215 extending between the proximal and distal ends 212, 214, and a lumen 217 defined at least partially by the body 215. In the illustrated embodiments, the lumen 217 has a cross sectional dimension that is between 0.5 millimeter and 1.5 millimeters, and more preferably, approximately 1 millimeter. The needle assembly 110 further includes a shaft 216 having a proximal end 218, a distal end 220, and a lumen 222 extending between the proximal and distal ends 218, 220. The proximal end 212 of the coring needle 200 is secured to the distal end 220 of the shaft 216. The puncture needle 202 has a proximal end 232, a distal end 234, a body 230 extending between the proximal and distal ends 232, 234, and a lumen 236 within the body 230. The lumen 236 has a cross sectional dimension sized for accommodating at least a portion of the coring needle 200, and for allowing the coring needle 200 to slide relative to the puncture needle 202. The distal end 234 of the puncture needle 202 has a sharp tip 250 for piercing tissue.

Figure 21B:
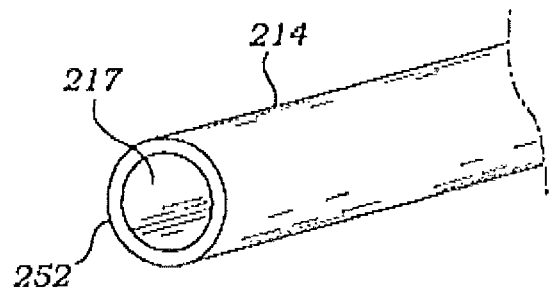
FIGS. 21B-21D illustrate variations of a distal end of the needle assembly of FIG. 21A in accordance with different embodiments.
Figure 21C:
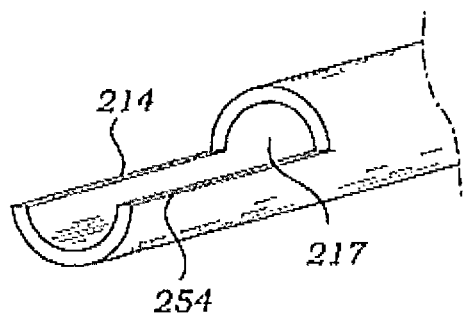
Figure 21D:
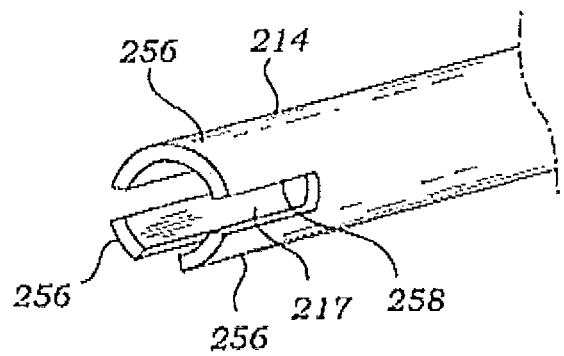

In the illustrated embodiments, the distal end 214 of the coring needle 200 has a tubular configuration (FIG. 21B). In such cases, the edge 252 of the coring needle 200 may have a sharp configuration for allowing the coring needle 200 to penetrate tissue. In other embodiments, the distal end 214 of the coring needle 200 may have an arc configuration (FIG. 21C). In such cases, the ends 254 of the arc portion may have a sharp configuration for allowing the coring needle 200 to cut tissue as the coring needle 200 is rotated about its axis. In further embodiments, the distal end 214 of the coring needle 200 can include a plurality of cutting portions 256, with each cutting portion 256 having a sharp edge 258 for cutting tissue (FIG. 21D). It should be noted that the distal end 214 of the coring needle 200 is not limited to the examples described previously, and that the distal end 214 can have other configurations in other embodiments, as long as it can core tissue.

The needle assembly 110 further includes a first engagement portion 238 and a second engagement portion 240. The first engagement portion 238 has a tubular configuration, and is secured to the shaft 216. The second engagement portion also has a tubular configuration, and is secured to the proximal end 232 of the puncture needle 202. proximal end 232 of the puncture needle 202. The first and the second engagement portions 238, 240 are sized and shaped to engage with corresponding components of the holding unit 109. It should be noted that the first and second engagement portions 238, 240 are not limited to the example of the configuration illustrated, and that the engagement portions 238, 240 can have other configurations in other embodiments. For example, in alternative embodiments, the engagement portion 238 does not have a tubular configuration. In such cases, the engagement portion 238 can be a structure that is secured to, or extends from, a surface of the shaft 216. Similarly, in other embodiments, the engagement portion 240 can be a structure that is secured to, or extends from, a surface of the puncture needle 202, and needs not have a tubular configuration. As shown in the figure, the needle assembly 110 also includes a connector 248 secured to the shaft 216. The connector 248 has a shape that resembles a sphere, but may have other shapes in other embodiments.

The plunger 204 has a proximal end 242 and a distal end 244. The plunger 204 is at least partially located within the lumen 217 of the coring needle 200, and is slidable relative to the coring needle 200. The needle assembly 110 further includes a spring 246 coupled to the plunger 204 for biasing the plunger 204 in a proximal direction relative to the coring needle 200. In the illustrated embodiments, the plunger 204 is described as a component of the needle assembly 110. In other embodiments, the plunger 204 is not a part of the needle assembly 110. For example, the plunger 204 may be a component of the positioning assembly 106.

Figure 22:
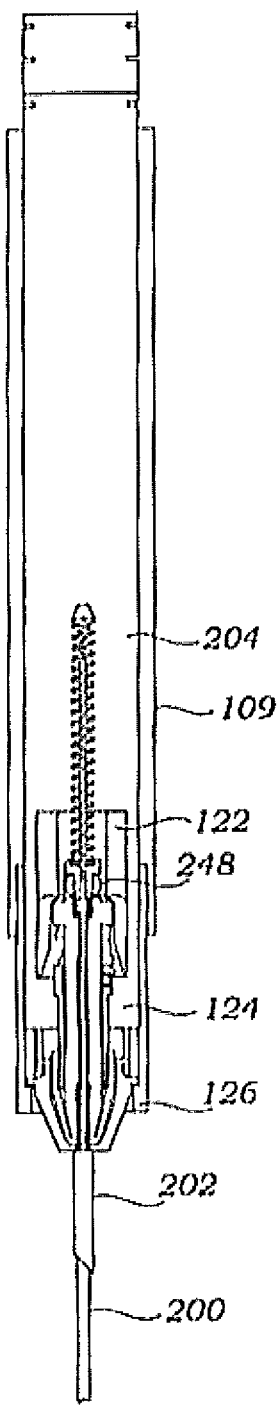
FIG. 22 illustrates the needle assembly of FIG. 21A being engaged with the holding unit of FIG. 20.

FIG. 22 illustrates the needle assembly 110 that has been engaged with the positioning assembly 106. When the needle assembly 110 is snapped onto the positioning assembly 106, the first engagement portion 122 of the holding unit 109 is engaged with the connector 248, the second engagement portion 124 is engaged with the first engagement portion 238 of the needle assembly 110, and the third engagement portion 126 is engaged with the second engagement portion 240 of the needle assembly. The connector 248 allows the needle assembly 110 to be detachably secured to the positioning assembly 106. The first engagement portion 122 of the holding unit 109 is coupled to the first positioner 107a. In some embodiments, the coring needle 200 is not translatable. In alternative embodiments, the first positioner 107a is configured to translate (e.g., advance or retract) the coring needle 200. The second engagement portion 124 of the holding unit 109 is coupled to the second positioner 107b, which is configured to rotate the coring needle 200 about its axis. The third engagement portion 126 of the holding unit 109 is coupled to the third positioner 107c, which is configured to translate (e.g., advance or retract) the puncture needle 202. In other embodiments, the second engagement portion 124 of the holding unit 109 may be coupled to both the first positioner 107a and the second positioner 107b. In such cases, the first positioner 107a is configured to translate the engagement portion 124 to thereby advance or retract the coring needle 200, and the second positioner 107b is configured to rotate the engagement portion 124 to thereby turn the coring needle 200 about its axis. In further embodiments, the second positioner 107b is not needed, and the needle assembly 110 does not include the engagement portion 238. In such cases, the positioning assembly 106 is not configured to rotate the coring needle 200, but to advance and retract the coring needle 200 in a back and forth trusting motion. In still further embodiments, the third positioner 107c is not needed, and the third engagement portion 126 is fixedly secured to the holding unit 109. In such cases, the puncture needle 202 may be positioned by the robotic arm 27, and the coring needle 200 may be positioned relative to the puncture needle 202 using the first positioner 107a.

When using the needle assembly 110 to harvest a follicular unit, the needle assembly 110 is first coupled to the positioning assembly 106. Such may be accomplished manually by snapping the needle assembly 110 onto the positioning assembly 106. Alternatively, the needle assembly 110 may be held upright by a stand (not shown). In such cases, the robotic arm 27 may be used to move the positioning assembly 106 to "grab" the needle assembly 110 from the stand. The camera(s) 28 may be used to provide information regarding a position of the needle assembly 110 to the processor 120, which controls the robotic arm 27 based on the information, thereby placing the positioning assembly in engagement position relative to the needle assembly 110.

Next, a treatment plan is inputted into the computer 120. In some embodiments, the treatment plan is a prescribed plan designed to transplant hair follicles from a first region (harvest region) to a target region (implant region). In such cases, the treatment plan may include one or more parameters, such as a number of hair follicles to be removed/implanted, location of harvest region, location of implant region, a degree of randomness associated with targeted implant locations, spacing between adjacent targeted implant locations, depth of follicle, depth of implant, patient identification, geometric profile of harvest region, geometric profile of implant region, marker location(s), and density of targeted implant locations. Various techniques may be used to input the treatment plan into the computer 120. In the illustrated embodiments, the treatment plan may be inputted using a user interface that includes a monitor 122 and a keyboard 124. Alternatively, the treatment plan may be inputted using a storage device, such as a diskette or a compact disk. In other embodiments, the treatment plan may be downloaded from a remote server. In further embodiments, the treatment plan may be inputted using a combination of the above techniques. For example, some parameters may be inputted into the computer 120 using a diskette, while other parameters may be inputted using the user interface. In some embodiments, one or more parameters of the treatment plan may be determined in real time (e.g., during a treatment session).

After the treatment plan has been inputted into the computer 120, the computer 120 then registers the treatment plan with a patient. In some embodiments, such may be accomplished by using the camera(s) 28 to identify one or more markers on the patient. The marker may be a reflector that is secured to the patient, an ink mark drawn on the patient, or an anatomy of the patient. The identified marker(s) may be used to determine a position and/or orientation of a target region on the patient.

Figure 23:
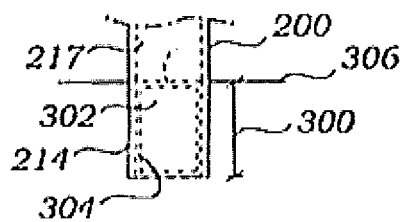
FIG. 23 illustrates a follicular unit being harvested by a coring needle in accordance with some embodiments.

In the illustrated embodiments, the treatment plan includes a position of the harvest region. Using input from the camera(s) 28, the computer 120 identifies the location of the harvest region on the patient, and a target follicular unit in the harvest region. The computer 120 then operates the robotic arm 27 to place the distal end 214 of the coring needle 200 next to the target follicular unit. In some embodiments, the coring needle 200 is positioned coaxial to the target follicular unit. Next, the coring needle 200 is used to harvest the target follicular unit 302 (FIG. 23). In some embodiments, such may be accomplished by activating a positioner within the positioning assembly 106 to rotate the coring needle 200. As the coring needle 200 is rotated, the coring needle 200 may be advanced distally (e.g., by activating another positioner within the positioning assembly 106, or by moving the positioning assembly 106 using the robotic arm 27). In other embodiments, the harvesting of the target follicle 302 unit may be accomplished by thrusting the coring needle 200 forward and backward. While the coring needle 200 is used to core out the follicular unit 302, the puncture needle 202 is located proximally away from the distal end 214 of the coring needle 200 to thereby prevent interference with the coring procedure. Such may be accomplished by advancing the coring needle 200 distally relative to the puncture needle 202, or alternatively, by retracting the puncture needle 202 proximally relative to the coring needle 200 (if the puncture needle 202 can be positioned).

When the distal end 214 of the coring needle 200 has been advanced within a prescribed depth 300, e.g., 5 millimeter, below a skin surface 306 (FIG. 23), the coring needle 200 is then retracted proximally to remove the coring needle 200 from the patient. In the illustrated embodiments, the camera(s) 28 may be used to monitor the coring process to thereby determine an amount of coring needle 200 that has been advanced below the skin surface 306. In some embodiments, the exterior of the coring needle 200 may include marker lines to thereby allow the camera(s) 28 or a physician to "see" how much of the coring needle 200 has been advanced into the patient. In some embodiments, surface friction at the interface between the follicular unit 302 and the interior surface 304 within the lumen 217 will hold the follicular unit 302 as the coring needle 200 is removed from the patient, thereby harvesting the follicular unit 302. In other embodiments, the interior surface 304 can be texturized (e.g., having one or more indents or protrusions) to thereby allow the distal end 214 to more easily hold onto the follicular unit 302 as the coring needle 200 is removed from the patient. In further embodiments, a proximal end of the needle assembly 110 may be coupled to a vacuum unit (not shown) located within the positioning assembly 106. In such cases, the vacuum unit creates a suction within the lumen 217 of the coring needle 200, to thereby pull the target follicular unit 302 away from its underlying tissue as the coring needle 200 is removed from the patient.

Figures 24A, 24B:
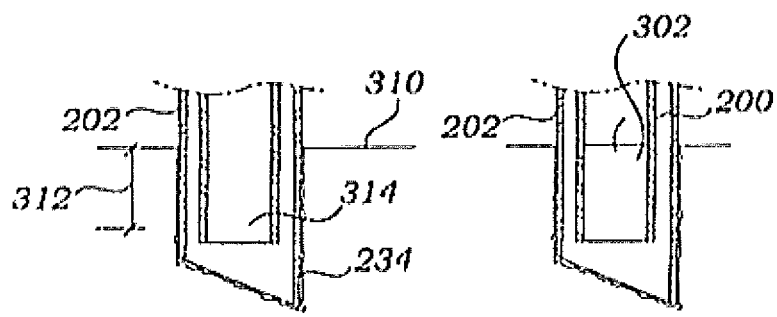
FIGS. 24A-24D illustrates a process for implanting a follicular unit in accordance with some embodiments.

After the follicular unit 302 has been harvested, the positioning assembly 106 then retracts the coring needle 200 proximally until the distal end 214 is proximal to the distal end 234 of the puncture needle 202. Alternatively, if the puncture needle 202 is positionable, the puncture needle 202 may be advanced distally until the distal end 234 is distal to the distal end 214 of the coring needle 200. Next, the computer 120 operates the robotic arm 27 to place the distal end 234 of the puncture needle 202 adjacent to a target location within an implant region of the patient as prescribed by the treatment plan. The puncture needle 202 is then advanced (e.g., by activating a positioner within the positioning assembly 106, or by moving the positioning assembly 106 distally towards the target location) to pierce through the skin 310 at the implant region (FIG. 24A). The puncture needle 202 is advanced until the penetrated depth 312 is at least equal to the coring depth 300. In some embodiments, the camera(s) 28 and the computer 120 may be used to determine an amount of the puncture needle 202 that has been advanced into the patient. For example, the puncture needle 202 may include a plurality of marker lines for allowing the camera(s) 28 or a physician to "see" how much of the puncture needle 202 has been inserted into the patient. As shown in the figure, the puncture needle 202 creates an opening 314 below the patient's skin 314, in which the follicular unit 302 may be placed.

Next, the coring needle 200, which contains the harvested follicular unit 302, is advanced within the lumen 236 of the puncture needle 202, until a top surface 320 of the follicular unit 302 is at or below the skin 310 at the implant region (FIG. 24B).

Figures 24C, 24D:
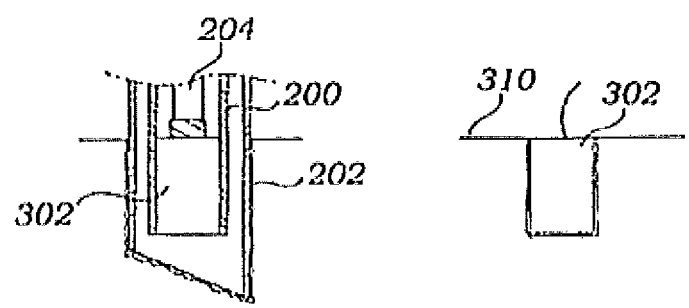

Next, the plunger 204 may be advanced distally (e.g., by using another positioner within the positioning assembly 106) until its distal end 244 engages with the follicular unit 302 located within the coring needle 200 (FIG. 24C). The puncture needle 202 and the coring needle 200 are then retracted proximally relative to the plunger 204, thereby leaving the follicular unit 302 implanted at the target location in the implant region (FIG. 24D). In other embodiments, the needle assembly 110 does not include the plunger 204. In such cases, a pressure generator (not shown) located within the positioning assembly 106 may be used to create a pressure within the lumen 217 of the coring needle 200, thereby pushing the follicular unit 302 towards the patient as the puncture needle 202 and the coring needle 200 is retracted. Such technique will cause the follicular unit 302 to dislodge from the coring needle 200 while the coring needle 200 is being removed from the patient.

After the first follicular unit 302 has been implanted in the implant region, the coring needle 200 is advanced distally until its distal end 214 is distal to the distal end 234 of the puncture needle 202. The computer 120 then operates the robotic arm 27 again to place the coring needle 200 next to another target follicular unit 302 to be harvested. The above described process is then repeated to harvest the next follicular unit 302, and to implant the follicular unit 302. The selection of the follicular unit 302 may be determined by the computer 120. For example, in some embodiments, based on a location and geometry of the prescribed harvest region, the computer 120 selects a follicular unit 302 only if it is within the prescribed harvest region. In some embodiments, the above process is repeated until a prescribed number of follicular units 302 have been implanted in the implant region, until a density of the implanted follicle units 302 reaches a prescribed density, or until there is no more available follicular unit 302 in the harvest region.

During the above harvesting and implanting process, the force sensor 100 monitors one or more force/moment component transmitted from the positioning assembly 106. For example, the force sensor 100 may monitor a force Fz, which has a directional vector that is approximately parallel to an axis of the coring needle 200. The sensed force Fz is transmitted to the computer 120, which determines whether a magnitude of the sensed force Fz is within an acceptable limit. In some embodiments, the computer 120 is configured (e.g., programmed) to stop a harvest process or an implant process if the sensed force Fz exceeds a prescribed limit, which may indicate that the coring needle 200 or the puncture needle 202 is pressing against the skull, for example. As such, the force sensor 100 provides a safety feature that prevents the coring needle 200 and the puncture needle 202 from injuring a patient in an unintended way.

Figure 25:
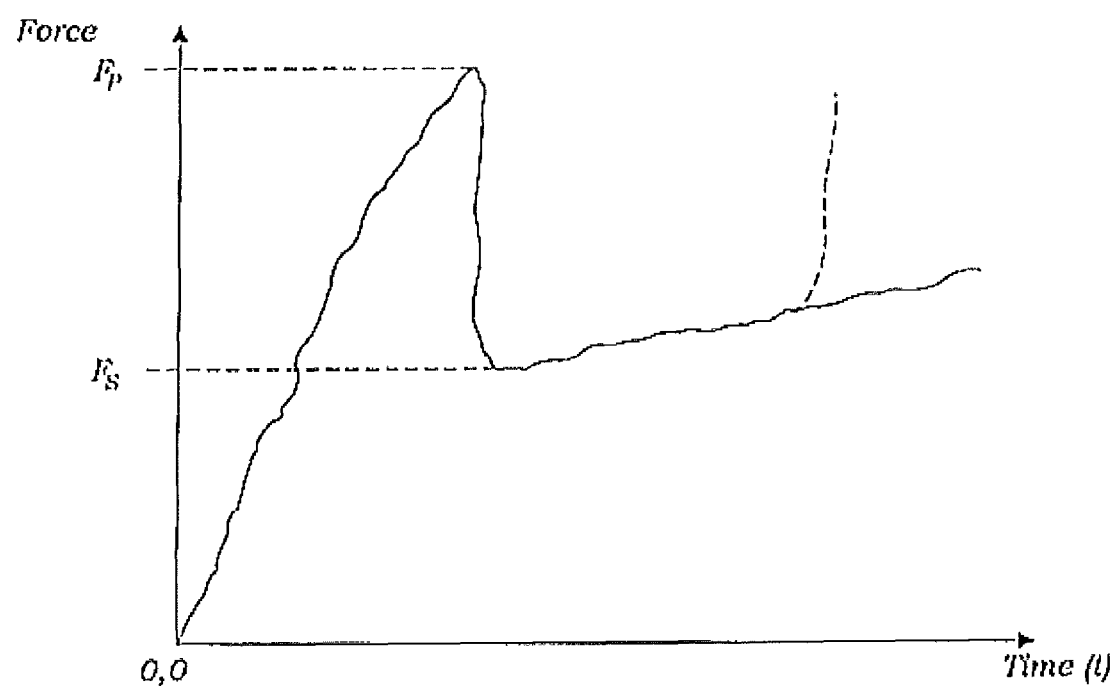
FIG. 25 illustrates a force diagram representing a force experienced by a coring needle in accordance with some embodiments.

In other embodiments, instead of, or in addition to, using the force sensor 100 as a safety feature, the force sensor 100 may also be used to control a positioning of the coring needle 200 and/or the puncture needle 202. As the coring needle 200 is being advanced through the skin and into tissue underneath the skin, the coring needle 200 experiences a force Fz, which represents a resistance encountered by the coring needle 200. FIG. 25 illustrates a force diagram that represents a force resistance Fz sensed by the coring needle 200 as the coring needle is advanced through the skin and into tissue. Such force Fz is transmitted by the various components within the positioning assembly 106 to the force sensor 100, which measures such force Fz and transmits the force data to the computer 120. Because the skin surface is relatively tough, initially, as the coring needle 200 pushes against skin, it will not immediately penetrates the skin, and will experience a force resistance Fz provided by the skin surface. The force resistance Fz increases from zero to a value Fp, at which point, the coring needle 200 penetrates through the skin. Because the tissue underneath the skin is relatively softer than the skin, the force resistance Fz experienced by the coring needle 200 will be less than Fp after the coring needle 200 penetrates the skin. As shown in FIG. 25, after the value Fp is reached, the force curve falls back to a second value Fs, which represents the force resistance sensed by the coring needle 200 after it has penetrated the skin surface. The force Fz will continue to increase from that point as the coring needle 200 continues to be advanced into the tissue. This is because as more portion of the coring needle 200 is advanced into the tissue, the coring needle 200 will contact more tissue that is underneath the skin, thereby increasing an amount of surface friction between the coring needle 200 and the tissue. In some cases, if the coring needle 200 hits a bone, the force diagram will result in a spike (shown in dotted line in the figure).

The computer 120 may be programmed to monitor the force curve being generated as the coring needle 200 is being advanced during the harvest process, and controls the coring needle 200 based on the force curve. For example, in some embodiments, the computer 120 activates a positioner in the positioning assembly 106 to advance the coring needle 200 at a first rate until a dip in the force curve is observed, indicating that the coring needle 200 has penetrated the skin. After that, the computer 120 then activates the positioner to advance the coring needle 200 at a second rate until a desired penetration depth is accomplished. In some embodiments, the first rate may be faster than the second rate.

Figure 26:
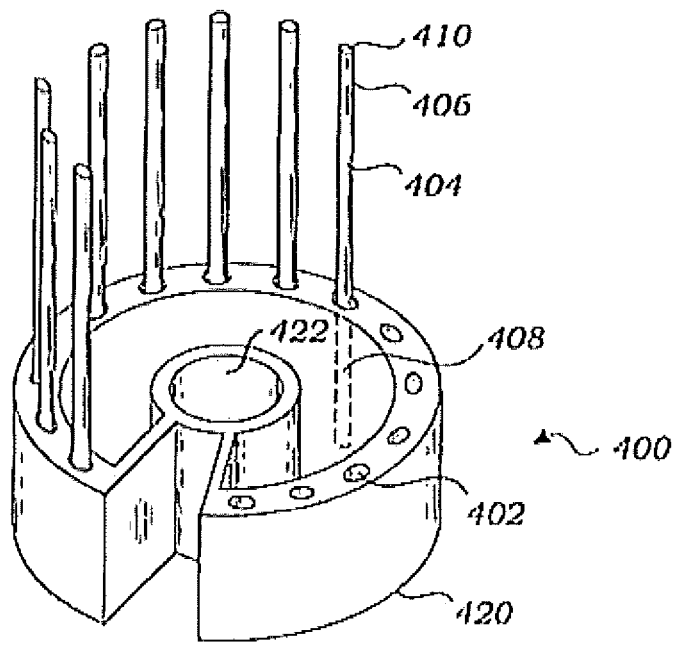
FIG. 26 illustrates a cartridge for holding a plurality of coring needles in accordance with some embodiments.

In the above embodiments, the same coring needle 200 is used to harvest and implant multiple follicular units 302. In other embodiments, multiple coring needles may be provided, wherein each of the coring needles may be used to harvest and implant one or more follicular units 302. FIG. 26 illustrates a needle cartridge 400 in accordance with some embodiments. The cartridge 400 has a plurality of slots or openings 402, each of which sized to accommodate a coring needle 404. Each of the coring needles 404 has a proximal end 406, a distal end 408, and a lumen 410 extending between the proximal and the distal ends 406, 408. The coring needle 404 has a similar configuration as the coring needle 200 described with reference to FIG. 21A. The slots 402 are located circumferentially near a periphery of the cartridge 400. Alternatively, the slots 402 may be arranged in a different configuration. For example, in other embodiments, the slots 402 may be arranged in a form of a matrix having N number of rows by M number of columns. In the illustrated embodiments, the cartridge 400 further has a bottom 420, which may be adapted for placement on a surface (e.g., the surface 36 shown in FIG. 1). The cartridge 400 also includes an engagement portion 422 configured (e.g., sized and shaped) for detachably securing to a component of the positioning assembly 106. The engagement portion 422 may be a slot/opening, a surface having a protrusion, or a connector device.

Figure 27:
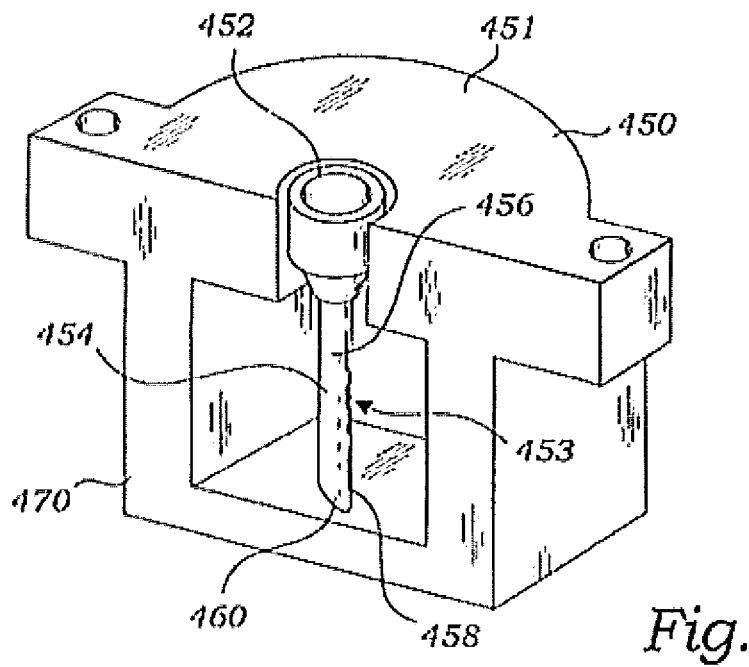
FIG. 27 illustrates a puncture needle holder in accordance with some embodiments.

FIG. 27 illustrates a puncture needle holder 450 for holding a puncture needle assembly 453 in accordance with some embodiments. The puncture needle holder 450 may be used with the cartridge 400. The puncture needle holder 450 includes a body 451 having an opening 452 for accommodating the puncture needle assembly 453. The puncture needle assembly 453 may be fixedly secured to the puncture needle holder 450, or alternatively, be slidably coupled to the puncture needle holder 450. The puncture needle assembly 453 includes a puncture needle 454 having a proximal end 456, a distal end 458, and a lumen 460 extending between the proximal and distal ends 456, 458. The puncture needle assembly 453 also includes an engagement portion 462 secured to the proximal end 456 of the puncture needle 454. The puncture needle 454 has a similar configuration as the puncture needle 202 described with reference to FIG. 21A. As shown in FIG. 27, a stand 470 may be provided to support the puncture needle holder 450.

Figure 28:
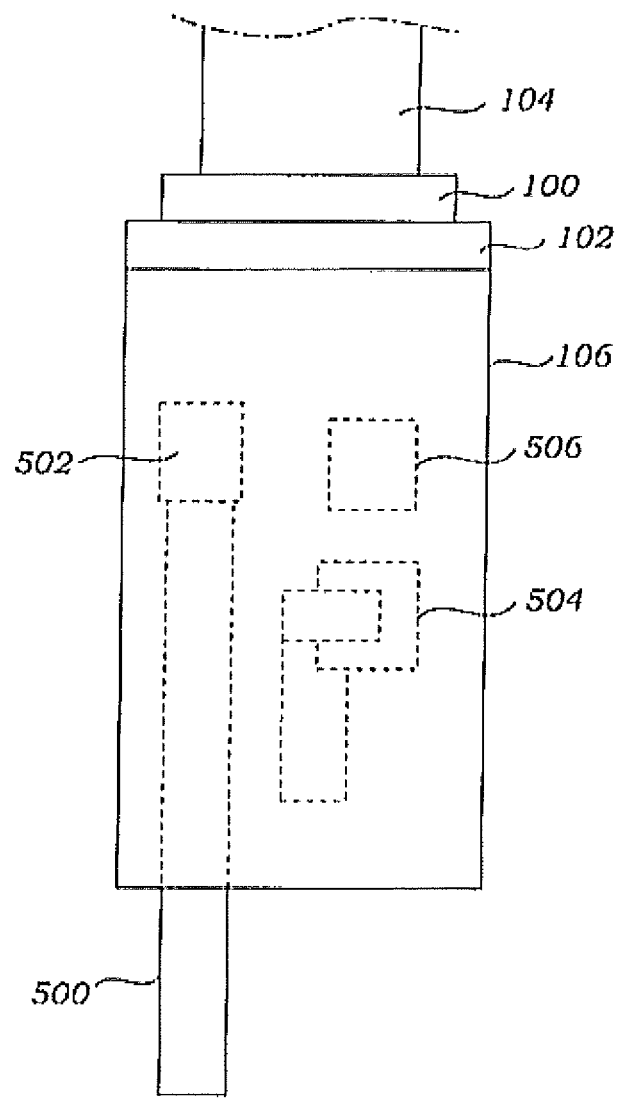
FIG. 28 illustrates a positioning assembly in accordance with other embodiments.

FIG. 28 illustrates a positioning assembly 106 in accordance with other embodiments. The positioning assembly 106 includes a cartridge holer 500, a positioner 502 for positioning the cartridge holder 500, a coring needle holder 504, and a positioner 506 for positioning the coring needle holder 504. In other embodiments, the positioning assembly 106 does not include the positioner 502, in which case, the cartridge holder 500 does not move relative to the positioning assembly 106 after the cartridge holder 500 is detachably coupled to the cartridge holder 500.

Figure 29A:
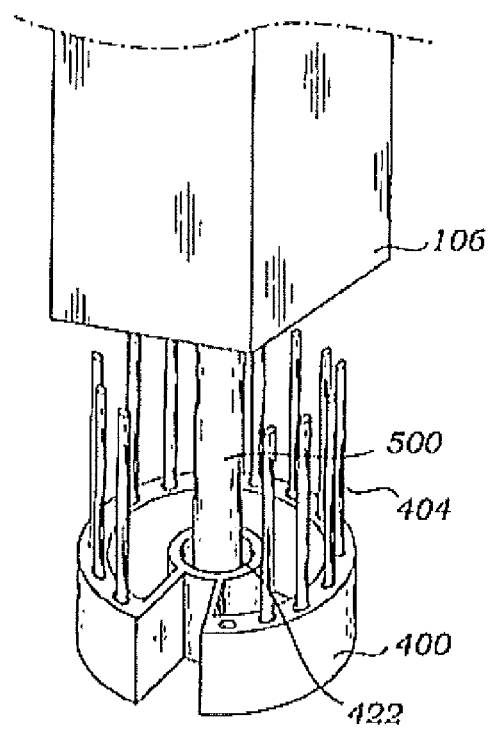
FIGS. 29A-29D illustrate a process of harvesting and implanting a follicular unit using the positioning assembly of FIG. 28, the cartridge of FIG. 26, and the puncture needle holder of FIG. 27 in accordance with some embodiments.

FIGS. 29A-29D illustrate a method of using the positioning assembly 106 of FIG. 28, the cartridge 400 of FIG. 26, and the puncture needle holder 250 of FIG. 27 to harvest and implant a follicular unit in accordance with some embodiments. First, the cartridge 400, with a plurality of coring needles 404 loaded therein, is placed on the support surface 36 next to the positioning assembly 106. The camera(s) 28 is then used to view the cartridge 400 and transmit image data to the computer 120 for processing. The computer 120 processes the image data to determine a position of the cartridge 400, and activates the robotic arm 27 to pick up the cartridge 400 based on the processing of the image data (FIG. 29A). In some embodiments, the computer 120 is configured to recognize a feature associated with the cartridge 400. For example, the cartridge 400 may have a marker attached thereto, in which case, the computer 120 is configured to determine the marker location. Various techniques may be employed to allow the robotic arm 27 to pick up the cartridge 400. In the illustrated embodiments, the cartridge holder 500 of the holder assembly 106 is shaped and sized to detachably mate with the engagement portion 422 of the cartridge 400. For example, if the engagement portion 422 comprises a slot, the cartridge holder 500 may be implemented as a snap-on extension that is configured to be inserted into the slot. In other embodiments, the cartridge holder 500 may include an electromagnetic device that generates a magnetic field using a current. In such cases, the engagement portion 422 of the cartridge 400 includes a magnet that can be coupled to the cartridge holder 500.

Figure 29B:
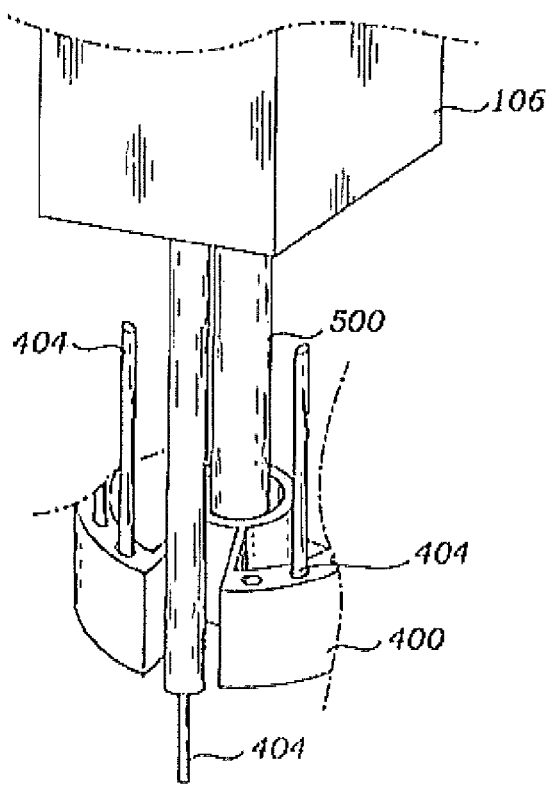

Next, the positioner 506 is activated to move the coring needle holder 504 so that the coring needle holder 504 engages with one of the coring needles 404. The coring needle holder 504 picks up the coring needle 404, and is moved to an operative position in the positioning assembly 106 at which the coring needle 404 may be positioned (e.g., rotated and/or advanced) for coring a follicular unit (FIG. 29B). The robotic arm 27 is then activated to move positioning assembly 106 such that the coring needle 404 at the operative position is adjacent to a target follicular unit, and the coring needle 404 is used to core the target follicular unit (e.g., by rotating the coring needle 404 using a motor (not shown), or by advancing and retracting the coring needle 404 in a thrusting action). The technique for coring the follicular unit is similar to that discussed previously. After a first follicular unit has been cored, the positioner 506 is activated to move the coring needle holder 504 to place the coring needle 404 back to the slot 402 of the cartridge 400. The positioner 506 then moves the coring needle holder 504 to pick up another empty coring needle 404 from another slot 402, and the process is repeated until all of the coring needles 404 have been used to harvest respective follicular units, or until a desired number of follicular units have been obtained.

In some embodiments, if the cartridge holder 500 is rotatable about its axis, the cartridge holder 500 may be rotated to place a coring needle 404 at a location from which the coring needle holder 504 may pick up and place back the coring needle 404.

Figure 29C:
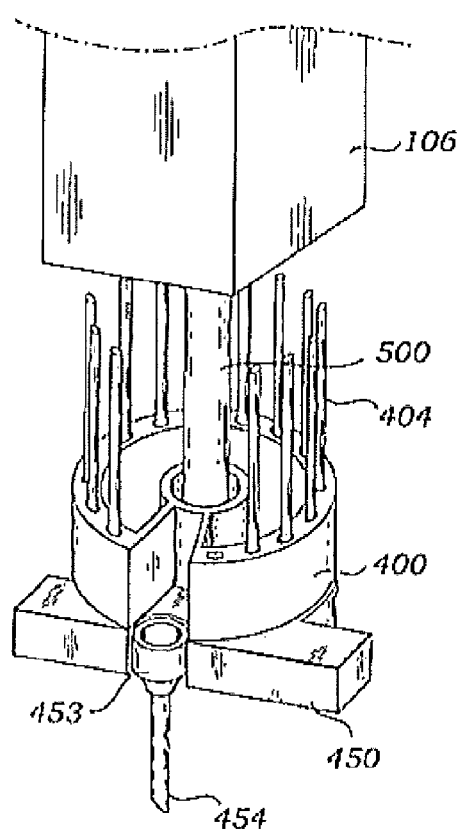

When a desired number of follicular units have been obtained, the robotic arm 27 is positioned to pick up the puncture needle holder 450 (FIG. 29C). In the illustrated embodiments, the puncture needle holder 450 is supported on the stand 470, which is placed on the support surface 36. Similar technique for picking up the cartridge 400 may be employed to pick up the puncture needle holder 450. For example, the camera(s) 28 and the computer 120 may be used to determine a position of the puncture needle holder 450, and the puncture needle holder 450 may be have an engagement portion (not shown) configured for detachably coupled to a component (not shown) of the positioning assembly 106.

Figure 29D:
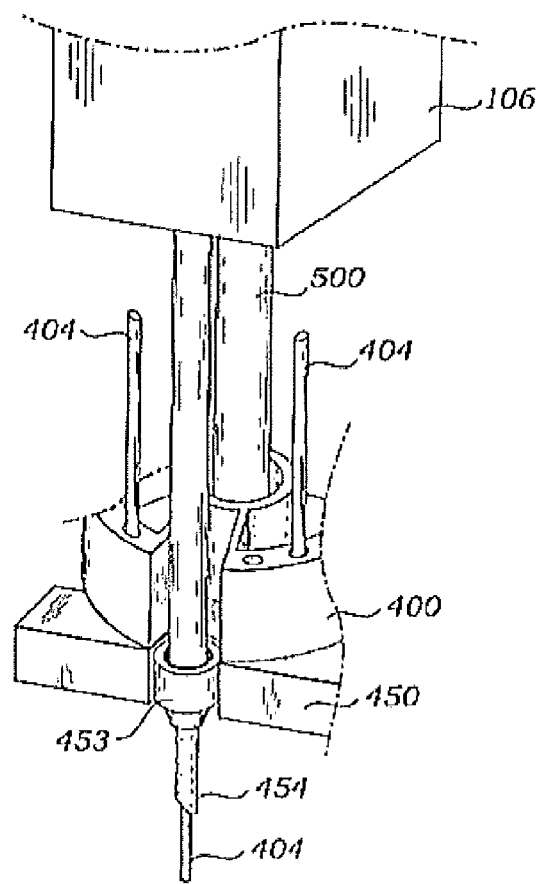

After the puncture needle holder 450 has been picked up by the positioning assembly 106, the robotic arm 27 is activated to move the positioning assembly 106 such that the coring needle 454 is adjacent to a target implant location. The positioner 506 then moves the coring needle holder 504 to pick up one of the coring needles 404 (which contains a harvested follicular unit), and moves the coring needle 404 such that it is at least partially within the lumen 460 of the puncture needle 454 (FIG. 29D). The coring needle 404 and the puncture needle 454 are then used to implant the follicular unit in the coring needle 404 using similar technique as that described previously. After the follicular unit has been implanted, the positioner 506 moves the coring needle holder 504 to place the empty coring needle 404 back to the cartridge 400, and the coring needle holder 504 picks up another coring needle 404 that has a harvested follicular unit. The above process is repeated to implant one or more additional follicular unit(s) at the implant region.

When all of the follicular units in the loaded coring needles 404 have been implanted in the implant region, if additional implanting is desired, the positioning assembly 106 places the puncture needle holder 450 back to its original location (e.g., on the stand 470), and decouples the puncture needle hnolder 450 from the positioning assembly 106. The cartridge 400 and the coring needles 404 are then used again to harvest additional follicular unit(s) from the harvest region, using the same process as that described.

Figure 30:
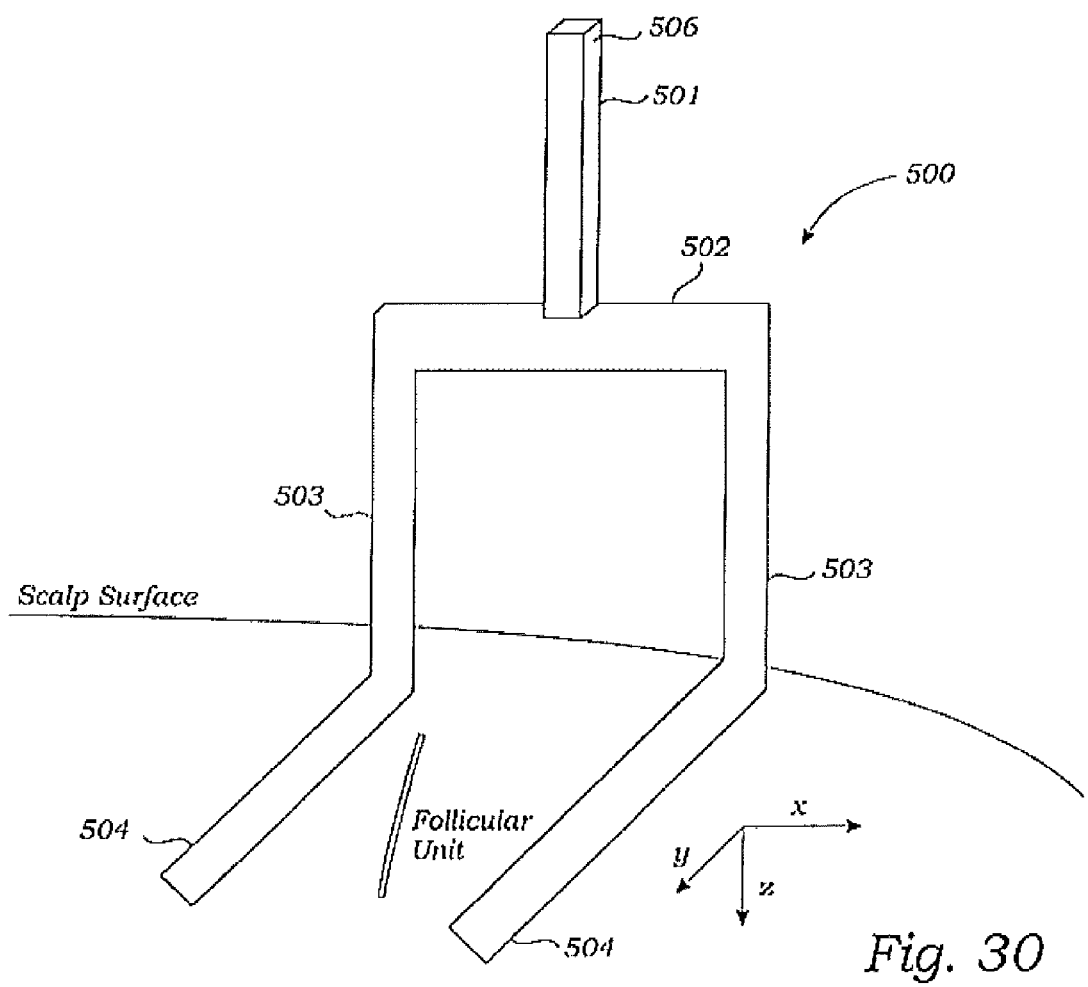
FIG. 30 illustrates a skin tensioner that can be used with embodiments described herein.

FIG. 30 illustrates a skin tensioner 500 that may be used with embodiments described herein. The skin tensioner 500 includes a shaft 501, a horizontal support 502, and two side tines 503. Each tine 503 includes a distal portion 504 for pressing against a skin surface. The proximal end 506 of the shaft 501 is configured (e.g., sized and shaped) to engage with an end-effector of the robotic hair transplant system. The horizontal support 502 includes a spring-loaded mechanism (not shown) that exerts a force along the x-axis, thereby causing the tines 503 to spread apart from each other. During use, the distal portions 504 of the tines 503 are positioned next to a follicular unit, with the follicular unit being between the two distal portions 504. The spring-loaded mechanism then spreads the tines 503 apart to thereby tension the skin. As a result, the hair shaft associated with the follicular unit may stand more erect relative to the scalp surface. In some cases, the skin tension may also serve to temporarily occlude vessels (e.g., capillaries) surrounding the follicular unit, thereby reducing bleeding during the harvesting of the follicular unit. The puncture needle and coring needle described herein would act between the distal portions 504 of the tines 503.

In embodiments of the invention, the attending physician or operator can specify where a follicular unit needs to be implanted and at what angle, i.e., its relative location (or "implantation site"), orientation, and depth. This specification of the location, orientation and/or depth of a hair follicle to be implanted may be carried out by a treatment planning system. Alternatively, during the implanting mode, when the camera(s) are viewing the recipient area of the scalp, the attending operator may use a user interface (e.g., a conventional computer mouse) to specify the implant location and/or position and/or orientation and/or implant depth. Alternatively, the operator can point to location on the scalp by placing a temporary fiducial, such as an ink mark or a pointer that can be visualized, identified, and measured by the image processing system. Further, orientation can be specified directly on the computer monitor as a combination of two angles, such as rotation about x-axis and a rotation about y-axis (assuming that z-axis is along the needle), or by placing an elongated pointer on the scalp, which the image processing system can visualize and measure the angles.

In any case, the control of the robotic arm now becomes two steps. First, based on the specification of the location and orientation of the implant location, the computer processor directs the robot to move the implant needle to the desired location and orientation. Second, the actual implantation takes place, either solely by actuating the mechanism, or by a combination of robotic movement and/or mechanism actuation, in which the desired implant depth is achieved. Another way of specifying the orientation of the implanted follicular unit is to have the system match to the orientation of the existing hairs in the area of the implant. The system, after moving the implantation needle to the implant location, visualizes and measures the orientation of the hair follicles in the neighborhood of the implant location, and uses that orientation as the specification for the implant. In the case of neighboring hairs having different orientations, the system may, for example, obtain a weighted average of the various orientations for implanting the follicular unit.

FIG. 31 illustrates an implant needle 550 in accordance with yet another embodiment, and which also may be used with other embodiments described herein. The implant needle 550 is configured to harvest and divide a follicular unit into a plurality of follicular sections (i.e., slices). It is believed that each of the follicular sections obtained from the single follicular unit using the needle 500 has the ability to regenerate into a new follicular unit when replanted in the patient's scalp, so long as the respective follicular section contains a sufficient quantity of follicular epithelial stem cells and the structural matrix of the collagenous sheath. For more information, reference is made to Jung-Chul Kim and Yung-Chul Choi, "Hair Survival of Partial Follicles: Implications for Pluripotent Stem Cells and Melanocyte Reservoir," which is published as Chapter 9C in the textbook "Hair Transplantion, Fourth Edition, Revised and Exped by Walter P. Unger and Ronald Shapiro (Marcel Dekker, Inc. 2004) and which is fully incorporated herein by reference.

The implant needle 550 includes a lumen 554 and three slots 552a-552c transverse to an axis of the implant needle 550. The proximal end (not shown) of the implant needle 550 may be coupled to a needle assembly or a positioner, as described herein. During use, the implant needle 550 is used to core and harvest a follicular unit 560 (FIG. 32A). After the follicular unit 560 has been harvested, cutting elements 564a-564c are then inserted into respective slots 552a-552c, thereby cutting the follicular unit 560 into a plurality of sections 562a-562d (FIG. 32B). Notably, slots 552a-552d are located so that the cuts are made at mid-section of the follicular unit, where the follicular epithelial stem cells are concentrated. Each cutting element 564a-c may be a plate having a sharp edge, or may have another configuration. In the illustrated embodiments, each cutting element 564a-c may include a channel 566 for delivering a fluid (e.g., culture nutrient) between the follicular sections 562.

After the follicular sections 562 have been created, the cutting elements 564 are then retracted. As the cutting elements 564 are being retracted, fluid containing culture nutrient may be delivered through channels 566 of respective cutting elements 564. After the cutting elements 564 have been completely removed from the lumen 554 of the implant needle 550, a tube 570 may be placed around the implant needle 550 to thereby prevent the fluid between the follicular sections 562 from escaping through the slots 552 (FIG. 32C). In some embodiments, the fluid may be a quick setting material, such as paraffin or a gel, which acts to encapsulate (i.e., protect) and stabilize the follicular sections, and helps ensure they are implanted in the scalp in the same orientation as in the donor follicle.

In some embodiments, the insertion of the cutting elements 564 into the lumen 554 may be performed simultaneously. In other embodiments, the bottom-most cutting element 564c may be inserted first, thereby pushing the remaining follicular unit 560 upward. Then the next bottom-most cutting element 564b is inserted, thereby pushing the remaining follicular unit 560 upward. The last cutting element 564a is then inserted. In other embodiments, instead of having three slots 552a-552c, the implant needle 550 may have more or less then three slots 552. In such cases, the number of cutting elements 564 would correspond with the number of slots 552 on the implant needle.

In some embodiments, a plunger (e.g., plunger 204) may be used to implant the follicular sections 562 at different target locations. For example, the plunger 204 may be advanced to push the follicular sections 562a-562d distally until the distal most follicular section 562d is outside the lumen 554 of the implant needle 550. The implant needle 550 is then moved to a different target location, and the plunger 204 is further advanced to push the next follicular section 562c out of the lumen 554. The process is repeated until all of the follicular sections 562a-562d have been implanted. In other embodiments, the distal most follicular section 562d (the follicular base) is discarded and is not used. In further embodiments, the proximal most follicular section 562a (the follicular top) is discarded and is not used.

The forgoing illustrated and described embodiments of the invention are susceptible to various modifications and alternative forms, and it should be understood that the invention generally, as well as the specific embodiments described herein, are not limited to the particular forms or methods disclosed, but to the contrary cover all modifications, equivalents and alternatives falling within the scope of the appended claims. By way of non-limiting example, it will be appreciated by those skilled in the art that the invention is not limited to the use of a robotic system, including a robotic arm, and that other automated and semi-automated systems that have a moveable arm assembly may be used for carrying and precisely positioning the respective camera(s) and harvesting/implanting needle assemblies adjacent the body surface.

What is claimed:

1. A system comprising:
    a procedure tool configured to perform a procedure on a body;
    one or more mechanisms configured to produce a combination movement of the procedure tool in response to control signals applied to the one or more mechanisms;
    a force sensor configured to measure a resistance force encountered by the procedure tool moving through a skin into tissue;
    an interface configured to allow input of a procedure treatment plan;
    a processor configured to process 1) images of the body surface and 2) the procedure treatment plan;
    a controller operatively associated with the one or more mechanisms,
    wherein the combination movement of the procedure tool comprises one or more movement parameters, the system is an automated image-guided system and the controller is configured to control one or more movements of the tool based at least in part on a) images processed by a processor, b) the procedure treatment plan and c) a force curve, the force curve being generated based on information provided by the force sensor as the tool is being moved.

2. The system of claim 1, wherein the one or more movement parameters includes speed and the controller is operatively coupled to and configured to control at least one of the one or more mechanisms to cause the procedure tool to move at two or more different speeds, or vary a speed of the movement of the tool during different times of a procedure.

3. The system of claim 1, wherein the combination movement comprises at least one or more of reciprocating backward and forward thrusting movement, an advancement movement, or a retraction movement.

4. The system of claim 1, wherein the combination movement produces at least one advance motion, at least one cutting motion, at least one rotating motion of the procedure tool, or a combination thereof.

5. The system of claim 1, wherein the combination movement comprises at least one translational movement and at least one rotational movement that are provided substantially simultaneously.

6. The system of claim 1, wherein the controller is further configured to terminate the procedure if the resistance force exceeds a predetermined limit.

7. The system of claim 1, wherein the one or more mechanisms comprise motors, cams, springs, an actuation system, or any suitable mechanism configured to provide at least a part of the combination movement.

8. The system of claim 1, wherein the controller is configured to adjust a rate of advancement of the procedure tool into the tissue at least partially based on information provided by the force sensor.

9. The system of claim 1, wherein the interface is configured to allow a user to provide input to specify at least one or more of a speed, an orientation, an angle, a depth of the tool advancement to achieve a desired depth, a spacing between tool insertion locations, a degree of randomness associated with a targeted insertion location, a geometric profile of a procedure region, a distance, or a density of the tool insertion locations.

10. The system of claim 1, further comprising a robotic arm, wherein the procedure tool is attached to the robotic arm.

11. The system of claim 10, wherein the combination movement is produced at least in part by movement of the robotic arm.

12. The system of claim 1, wherein the procedure tool comprises one or more marker lines and wherein the controller is configured to determine how much the procedure tool has been advanced into a tissue.

13. The system of claim 1, wherein the controller is configured to assess when a dip in the force curve is reached, and is further configured to activate the one or more mechanisms to change one of the movement parameters, when the dip is reached.

14. The system of claim 1, wherein the procedure tool is a tissue removal tool, a hair removal tool, a laser, a needle, a punch, a hair harvesting tool, a hair implantation tool, a hair transplantation tool, a tattoo tool, a tattoo removal tool, or a biopsy cannula.

15. The system of claim 1, wherein the procedure comprises diagnostic medical procedures, therapeutic medical procedures, cosmetic procedures, application of laser or radio frequency energy, tattooing, tattoo removal, tissue removal, biopsy, hair removal, hair transplantation, face lift, or injections.

16. The system of claim 1, further comprising an air jet configured for directing an air stream at a body surface on which the procedure tool is to be used.

17. The system of claim 1, further comprising a mechanism configured to provide suction.

18. The system of claim 1, further comprising a holding unit for engagement with the procedure tool, wherein the holding unit is configured to accommodate the one or more mechanisms and engage the procedure tool.

19. A method of operating a procedure tool, the method comprising:
   using a processor to 1) process images of a body surface and 2) to automatically apply a procedure treatment plan;
   applying control signals to one or more mechanisms to produce a combination movement of a procedure tool, the combination movement comprises one or more movement parameters;
   using a force sensor to measure a resistance force encountered by the procedure tool moving through a skin into tissue;
   generating a force curve based on information provided by the force sensor;
   automatically determining without relying on movement of hands of an operator whether to adjust one or more movements parameters of the combination movement of the procedure tool based at least in part on a) the procedure treatment plan and b) the force curve.

20. The method of claim 19, comprising providing for an input of the treatment plan with a use of a monitor, a keyboard, a storage device, or downloading via a remote server, or a combination of any of the above.

21. The method of claim 19, comprising aligning the procedure tool positioned on a moveable arm with a location or an object on the body surface and applying a laser or radio frequency energy to the location or the object.

22. The method of claim 19, comprising identifying position and orientation of a plurality of follicular units in a region of interest on the body surface and removing some or all of the identified follicular units.

23. The method of claim 19, comprising using a force sensor to control a positioning of the procedure tool.

24. A system comprising:
   a procedure tool configured to perform a procedure on a body;
   one or more mechanisms configured to produce a combination movement of the procedure tool in response to control signals applied to the one or more mechanisms;
   a force sensor configured to measure a resistance force encountered by the procedure tool moving through a skin into tissue;
   an interface configured to allow input of a procedure treatment plan, wherein the procedure treatment plan comprises one or more movement parameters of the procedure tool;
   a controller operatively associated with the one or more mechanisms, the controller configured to control automatically one or more movements of the tool based at least in part on a) the procedure treatment plan and b) a force curve, the force curve being generated based on information provided by the force sensor as the tool is being moved.

25. The system of claim 24, wherein the procedure tool is a tissue removal tool, a hair removal tool, a laser, a needle, a punch, a hair harvesting tool, a hair implantation tool, a hair transplantation tool, a tattoo tool, a tattoo removal tool, or a biopsy cannula.

* * * * *